(12) United States Patent
Li et al.

(10) Patent No.: US 7,850,959 B2
(45) Date of Patent: Dec. 14, 2010

(54) METHODS AND COMPOSITIONS FOR TREATING CONDITIONS INVOLVING ABNORMAL ANGIOGENESIS

(75) Inventors: Jian Li, West Roxbury, MA (US); Jue-Lon Shie, Acton, MA (US); Roger J. Laham, Brookline, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 732 days.

(21) Appl. No.: 10/575,127

(22) PCT Filed: Oct. 12, 2004

(86) PCT No.: PCT/US2004/033735

§ 371 (c)(1),
(2), (4) Date: Jun. 11, 2007

(87) PCT Pub. No.: WO2005/034881

PCT Pub. Date: Apr. 21, 2005

(65) Prior Publication Data

US 2008/0138330 A1    Jun. 12, 2008

Related U.S. Application Data

(60) Provisional application No. 60/510,437, filed on Oct. 10, 2003.

(51) Int. Cl.
*A61K 38/00* (2006.01)
*A61K 48/00* (2006.01)
*C12N 15/00* (2006.01)
*C12N 15/06* (2006.01)
*C12N 15/07* (2006.01)

(52) U.S. Cl. .......................... 424/93.21; 514/2; 514/21; 514/44 R; 435/455

(58) Field of Classification Search ........................ None
See application file for complete search history.

(56) References Cited

U.S. PATENT DOCUMENTS

2002/0142457 A1* 10/2002 Umezawa et al. ........... 435/366

OTHER PUBLICATIONS

Stewart et al. Cloning of Human RTEF-1, a Transcriptional Enhancer Factor-1-Related Gene Preferentially Expressed in Skeletal Muscle: Evidence for an Ancient Multigene Family. Genomics, vol. 36, pp. 68-76, 1996.*
Ueyama et al. Identification of the functional domain in the transcription factor RTEF-1 that mediates alpha 1-adrenergic signaling in hypertrophied cardiac myocytes. Journal of Biological Chemistry, vol. 275, pp. 17476-17480, 2000.*
Burglin, TR. The TEA domain: a novel, highly conserved DNA-binding motif. Cell, vol. 66, pp. 11-12, Jul. 1991.*
Gupta et al. Human studies of angiogenic gene therapy. Circulation Research, vol. 105, No. 8, pp. 724-736, Oct. 2009.*
Strayer, DS. Gene therapy using SV40-derived vectors: what does the future hold? Journal of Cellular Physiology, vol. 181, pp. 375-384, 1999.*
Ehrhardt et al. Episomal vectors for gene therapy. Current Gene Therapy, vol. 8, pp. 147-161, 2008.*
Strayer et al. What can SV40-derived vectors do for gene therapy? Current Opinion in Molecular Therapeutics, vol. 4, No. 4, pp. 313-323, Aug. 2002.*
Hewson. RNA viruses: emerging vectors for vaccination and gene therapy. Molecular Medicine Today, vol. 6, pp. 28-35, Jan. 2000.*
Entry for TEAD 4 TEA domain family member 4 [*Homo sapiens*], GeneID: 7004, printed from Entrez Gene (www.ncbi.nlm.nih.gov) on Oct. 23, 2009 as pp. 1/7 to 7/7.*
GenBank Accession No. NP_003204, GI: 4507427, publicly available Oct. 2000, printed as pp. 1-2.*

* cited by examiner

*Primary Examiner*—Jennifer Dunston
(74) *Attorney, Agent, or Firm*—Clark & Elbing LLP; Kristina Bieker-Brady; Todd Armstrong

(57) ABSTRACT

The present invention features methods and compositions for preventing, reducing, or treating hypoxia and pathological disorders involving abnormal angiogenesis (e.g., conditions involving decreases or increases in blood flow, respectively). Where an increase in angiogenesis is desired, the mammal being treated for an ischemic condition is provided with Related Transcriptional Enhancer Factor-1 (RTEF-1; as a recombinant polypeptide or as an expression vector) sufficient to increase expression of VEGF, FGFR, or COX-2. This results in a concomitant increase in angiogenesis. Conversely, a mammal being treated for a hypervascular condition is administered a composition that reduces the levels of RTEF-1, thereby reducing the expression of VEGF, FGFR, or COX-2, which results in a decrease in angiogenesis. Also disclosed are screening methods that make use of RTEF-1 for the identification of novel therapeutics for the treatment, prevention, or reduction of pathological disorders involving hypoxia or abnormal angiogenesis, namely, ischemic or hypervascular conditions.

6 Claims, 13 Drawing Sheets

```
1    megtagtits newssptspe gstasggsqa ldkpidndge gvwspdieqs fqealaiypp
61   cgrrkiilsd egkmygrnel iaryiklrtg ktrtrkqvss hiqvlarrka reigaklkdq
121  aakdkalqsm aamssaqiis atafhssmrl argpgrpavs gfwggalpgq aetshdvkpf
181  sqqtyavqpp lplpgfespa gpapspsapp appwqgrrrg ssklwmlefs afleqqdpd
241  tynkhlfvhi gqsspsylrp yleavdirqi ydkfpekkgg lkdlfergps nafflvkfwa
301  dlntniedeg ssfygvssqy espenmiitc stkvcsfgkq vvekveteya ryenghysyr
361  ihrsplceym infihklkhl pekymmnsvl enftilqvvt nrdtqetllc iayvfevsas
421  ehgaqhhiyr lvke
```

FIGURE 13

SEQUENCE LISTING

<160> NUMBER OF SEQ ID NOS: 7

<210> SEQ ID NO 1
<211> LENGTH: 12
<212> TYPE: DNA

<213> ORGANISM: Artificial Sequence
<220> FEATURE:
<223> OTHER INFORMATION: synthesis

<400> SEQUENCE: 1
tttttttttt tt                                                              12

<210> SEQ ID NO 2
<211> LENGTH: 25
<212> TYPE: DNA
<213> ORGANISM: Artificial Sequence
<220> FEATURE:
<223> OTHER INFORMATION: synthetic

<400> SEQUENCE: 2
gctgaggctc gcctgtcccc gcccc                                                25

<210> SEQ ID NO 3
<211> LENGTH: 25
<212> TYPE: DNA
<213> ORGANISM: Artificial Sequence
<220> FEATURE:
<223> OTHER INFORMATION: synthesis

<400> SEQUENCE: 3
caaattccag caccgagcgc cctgg                                                25

<210> SEQ ID NO 4
<211> LENGTH: 50
<212> TYPE: DNA
<213> ORGANISM: Artificial Sequence
<220> FEATURE:
<223> OTHER INFORMATION: synthetic

<400> SEQUENCE: 4
tgtccccgcc ccccggggcg ggccggggc ggggtcccgg cggggcggag                      50

<210> SEQ ID NO 5
<211> LENGTH: 28
<212> TYPE: DNA
<213> ORGANISM: Artificial Sequence
<220> FEATURE:
<223> OTHER INFORMATION: synthetic

<400> SEQUENCE: 5
agcgccgggt gggagtgaga gagcgagc                                             28

<210> SEQ ID NO 6
<211> LENGTH: 30
<212> TYPE: DNA
<213> ORGANISM: Artificial Sequence
<220> FEATURE:
<223> OTHER INFORMATION: synthetic

<400> SEQUENCE: 6
gtgggactag cgccgggtgg gagtgagaga                                           30

<210> SEQ ID NO 7
<211> LENGTH: 434
<212> TYPE: PRT
<213> ORGANISM: Artificial Sequence
<220> FEATURE:
<223> OTHER INFORMATION: synthetic

<400> SEQUENCE: 7

Met Glu Gly Thr Ala Gly Thr Ile Thr Ser Asn Glu Trp Ser Ser Pro

-continued

```
1               5                   10                  15

Thr Ser Pro Glu Gly Ser Thr Ala Ser Gly Gly Ser Gln Ala Leu Asp
                20                  25                  30

Lys Pro Ile Asp Asn Asp Gly Glu Gly Val Trp Ser Pro Asp Ile Glu
                35                  40                  45

Gln Ser Phe Gln Glu Ala Leu Ala Ile Tyr Pro Pro Cys Gly Arg Arg
50                  55                  60

Lys Ile Ile Leu Ser Asp Glu Gly Lys Met Tyr Gly Arg Asn Glu Leu
65                  70                  75                  80

Ile Ala Arg Tyr Ile Lys Leu Arg Thr Gly Lys Thr Arg Thr Arg Lys
                85                  90                  95

Gln Val Ser Ser His Ile Gln Val Leu Ala Arg Arg Lys Ala Arg Glu
                100                 105                 110

Ile Gln Ala Lys Leu Lys Asp Gln Ala Ala Lys Asp Lys Ala Leu Gln
                115                 120                 125

Ser Met Ala Ala Met Ser Ser Ala Gln Ile Ile Ser Ala Thr Ala Phe
                130                 135                 140

His Ser Ser Met Arg Leu Ala Arg Gly Pro Gly Arg Pro Ala Val Ser
145                 150                 155                 160

Gly Phe Trp Gln Gly Ala Leu Pro Gly Gln Ala Glu Thr Ser His Asp
                165                 170                 175

Val Lys Pro Phe Ser Gln Gln Thr Tyr Ala Val Gln Pro Pro Leu Pro
                180                 185                 190

Leu Pro Gly Phe Glu Ser Pro Ala Gly Pro Ala Pro Ser Pro Ser Ala
                195                 200                 205

Pro Pro Ala Pro Pro Trp Gln Gly Arg Arg Arg Gly Ser Ser Lys Leu
                210                 215                 220

Trp Met Leu Glu Phe Ser Ala Phe Leu Glu Gln Gln Asp Pro Asp
225                 230                 235                 240

Thr Tyr Asn Lys His Leu Phe Val His Ile Gly Gln Ser Ser Pro Ser
                245                 250                 255

Tyr Leu Arg Pro Tyr Leu Glu Ala Val Asp Ile Arg Gln Ile Tyr Asp
                260                 265                 270

Lys Phe Pro Glu Lys Lys Gly Gly Leu Lys Asp Leu Phe Glu Arg Gly
                275                 280                 285

Pro Ser Asn Ala Phe Phe Leu Val Lys Phe Trp Ala Asp Leu Asn Thr
                290                 295                 300

Asn Ile Glu Asp Glu Gly Ser Ser Phe Tyr Gly Val Ser Ser Gln Tyr
305                 310                 315                 320

Glu Ser Pro Glu Asn Met Ile Ile Thr Cys Ser Thr Lys Val Cys Ser
                325                 330                 335

Phe Gly Lys Gln Val Val Glu Lys Val Glu Thr Glu Tyr Ala Arg Tyr
                340                 345                 350

Glu Asn Gly His Tyr Ser Tyr Arg Ile His Arg Ser Pro Leu Cys Glu
                355                 360                 365

Tyr Met Ile Asn Phe Ile His Lys Leu Lys His Leu Pro Glu Lys Tyr
                370                 375                 380

Met Met Asn Ser Val Leu Glu Asn Phe Thr Ile Leu Gln Val Val Thr
385                 390                 395                 400
```

```
                                -continued

Asn Arg Asp Thr Gln Glu Thr Leu Leu Cys Ile Ala Tyr Val Phe Glu
            405                 410                 415

Val Ser Ala Ser Glu His Gly Ala Gln His His Ile Tyr Arg Leu Val
            420                 425                 430

Lys Glu
```

METHODS AND COMPOSITIONS FOR TREATING CONDITIONS INVOLVING ABNORMAL ANGIOGENESIS

CROSS-REFERENCE TO RELATED APPLICATIONS

This application is the National Stage of International Application No. PCT/US2004/033735, filed Oct. 12, 2004, and claims benefit of U.S. Provisional Application No. 60/510,437, filed Oct. 10, 2003, each of which is hereby incorporated by reference.

STATEMENT AS TO FEDERALLY FUNDED RESEARCH

This invention was made with Government support under grant number HL063609 awarded by The National Institutes of Health. The Government has certain rights in the invention.

FIELD OF THE INVENTION

In general, the present invention features methods and compositions for increasing or decreasing angiogenesis. The invention is useful for the treatment, prevention, or reduction of conditions involving abnormal angiogenesis, namely ischemic and hypervascular conditions.

BACKGROUND OF THE INVENTION

Angiogenesis, the growth of new blood vessels, is a complex process involving the disruption of vascular basement membranes, the migration and proliferation of endothelial cells, and the subsequent formation and maturation of blood vessels. In cases in which there is excessive or insufficient angiogenesis, various pathological disorders arise including, for example, ischemic myocardial conditions, psoriasis, and peripheral vascular conditions.

Several mediators are known to positively or negatively regulate the angiogenic process. The administration of such mediators has therefore been suggested as a therapeutic strategy to either promote or reduce vascularization for the treatment of angiogenic disorders. Given that its cognate receptor is expressed almost exclusively on vascular endothelial cells, vascular endothelial growth factor (VEGF) is one of the most promising angiogenic ligands targeted for therapeutic purposes. In this regard, VEGF receptors are typically upregulated under ischemic conditions and consequently, the administration of recombinant VEGF augments the development of collateral vessels and improves the function of peripheral and myocardial ischemic tissues.

Another polypeptide factor which directly influences the migratory and proliferative activity of human endothelial cells and which is recognized as a mediator of human angiogenesis is fibroblast growth factor (FGF). FGF is a potent human endothelial cell mitogen which increases the survival and proliferation of human endothelial cells. FGF activity also results in an increase in skeletal and smooth muscle growth, neurogenesis, and organ/tissue repair.

Cyclooxygenase 2 (COX-2) is another factor that is involved in normal angiogenesis, as well as tumor-associated angiogenesis, tumor growth, and tumor metastasis. COX-2 is involved in the formation of prostanoids from arachidonic acid and is induced in response to a wide range of cellular signals in normal tissues.

Increasing angiogenesis when desirable and decreasing angiogenesis when undesirable, e.g., by modulating the activity of angiogenic factors, such as VEGF, continues to pose a significant challenge. The half-life of VEGF protein, e.g., is extremely short and the administration of high doses of VEGF is often associated with hypotension. Furthermore, the systemic administration of VEGF can cause the promiscuous induction of angiogenesis in healthy host tissues and as a result, cause blindness, increase the aggressiveness of tumor cells, and lead to a multitude of other negative side-effects. On the other hand, if VEGF is delivered in insufficient amounts, angiogenesis is not induced and thus, no significant therapeutic benefit is achieved.

Thus, there exists a need for an effective method of both inducing and inhibiting angiogenesis in a target tissue.

SUMMARY OF THE INVENTION

The present invention is based on our discovery that Hypoxia-induced Related Transcriptional Enhancer Factor-1 (RTEF-1) binds to the GC-rich regions of the Vascular Endothelial Growth Factor (VEGF) promoter (e.g., in endothelial cells), the Fibroblast Growth Factor Receptor (FGFR) promoter, and the CycloOXogenase (COX)-2 promoter, and in doing so, induces the expression of VEGF, FGFR, and COX-2, respectively. The methods and compositions of the present invention are therefore useful to treat, reduce, or prevent conditions caused by hypoxia, and can be used to promote or inhibit angiogenesis by increasing or decreasing, respectively, blood vessel growth in a mammal. Also disclosed are screening methods useful for the identification of candidate compounds for increasing or decreasing angiogenesis.

In a first aspect, the invention features methods for treating or reducing hypoxia in a mammal by providing to the mammal a therapeutically effective amount of Related Transcriptional Enhancer Factor-1 (RTEF-1) protein (e.g., using cell therapy methods, such as microinjection or transduction) or a fragment thereof that retains biological activity (e.g., the ability to bind to the promoter region of VEGF, FGFR, and COX-2 and to upregulate VEGF, FGFR, and COX-2 expression levels). Optionally, the RTEF-1 is provided to the mammal by means of a nucleic acid molecule that encodes RTEF-1 in a therapeutically effective amount. Typically, the RTEF-1 is provided either as a polypeptide or as a nucleic acid into cells within or adjacent to ischemic tissue. In an embodiment, the method increases angiogenesis in the mammal.

The invention also features a method of treating or reducing hypoxia in a mammal by providing the mammal a cell, tissue, or organ that contains RTEF-1 in a therapeutically effective amount. Desirably, such cell, tissue, or organ expresses at least 10%, 20%, 30%, 40%, 50%, 60%, 70%, 80%, 85%, 90%, 95%, 100%, or even more than 100% or more RTEF-1 protein relative to a control cell, tissue, or organ. In an embodiment, the cell, tissue, or organ can be provided (e.g., ex vivo) with an RTEF-1 polypeptide or a nucleic acid molecule encoding RTEF-1. The cell, tissue, or organ may be from any organ (e.g., a heart, liver, muscle, lung, pancreas, brain, skin, kidney, or eye) from an autologous source or from an allogeneic donor animal. Exemplary cells that may be used according to the invention include myocytes, fibroblasts, myoblasts, endothelial cells, cardiomyocytes, cardioblasts, and smooth muscle cells. The cells, tissues, or organs of the invention are typically provided within or adjacent to ischemic tissue. For example, a mammal diagnosed with a myocardial infarct may be provided with cardiomyocytes (that have been genetically engineered to overexpress RTEF-1) within ischemic tissues. In an embodiment, the method results in an increase in angiogenesis in the mammal.

In all foregoing aspects of the invention, the RTEF-1 of the invention has angiogenic activity and increases VEGF, FGFR, or COX-2 expression by at least 10%, 20%, 30%, 40%, 50%, 60%, 70%, 80%, 85%, 90%, 95%, 100%, or even more than 100% relative to an untreated control. By increasing VEGF expression, the RTEF-1 increases angiogenesis by at least 10%, 20%, 30%, 40%, 50%, 60%, 70%, 80%, 85%, 90%, 95%, 100%, or even more than 100% above control levels as measured by any method known in the art or described herein. Desirably, administration of RTEF-1 increases collateral blood vessel formation, improves abnormal cardiac function, or increases contractility of heart muscle. The RTEF-1 of the invention is substantially identical (having at least 10%, 20%, 30%, 40%, 50%, 60%, 70%, 80%, 85%, 90%, 95%, 100% sequence identity) to the naturally occurring RTEF-1, such as the human RTEF-1 (Accession Number AAC50763), mouse RTEF-1 (Accession Number Q62296), or chick RTEF-1 (Accession Number P48984), and includes naturally occurring variants of RTEF-1, such as those containing naturally occurring mutations or polymorphisms.

In preferred embodiments, RTEF-1 fragments for use in the invention comprise at least 30 amino acids, preferably 50 amino acids, more preferably 100 amino acids, and most preferably 200 amino acids or more and retain the ability to bind to the VEGF, FGFR, or COX-2 promoter region and to upregulate VEGF, FGFR, or COX-2 mRNA or protein levels in the cell or target tissue expressing the RTEF-1 fragment.

According to this invention, when provided as a nucleic acid molecule, the RTEF-1 is encoded within an expression vector, such as plasmid or a viral vector (e.g., adenovirus, retrovirus, adeno-associated virus vector, herpes simplex virus, SV40 vector, polyoma virus vector, papilloma virus vector, picornavirus vector, or vaccinia virus vector). If desired, the RTEF-1-encoding nucleic acid molecule is under the control of a tissue-specific promoter. Consequently, RTEF-1 expression may be specific to any desired cell type including, for example, endothelial cells, cardiomyocytes, skin cells, hepatocytes, myocytes, adipocytes, and fibroblasts, as well as any cell type in any tissue in which the RTEF-1 is to be provided.

The methods of the present invention are therefore useful for the treatment, reduction, or prevention of ischemic conditions including, for example, cardiac infarction, chronic coronary ischemia, chronic lower limb ischemia, stroke, cerebral ischemia, peripheral vascular disease, and myocardial ischemia. Other conditions amenable to treatment include myocardial infarcts, unstable angina, cardiac hypertrophy, arrhythmia, cardiomyopathy, angina pectoris, atherosclerosis, arteriosclerosis, a complication of diabetes, restenosis, organ hypertrophy, organ hyperplasia, septic shock, inflammatory disease, and myocardial dysfunction.

The methods of the invention may also be used prophylactically. Consequently, a mammal may be provided with the compositions of the invention in anticipation of an ischemic condition, such as a surgical procedure (e.g., coronary bypass surgery, vascular surgery, percutaneous transluminal coronary angioplasty, percutaneous transluminal coronary intervention, or organ transplantation) or trauma. Typically, the mammal is provided with the RTEF-1 within three days before or after such an ischemic condition has occurred.

In an embodiment of all of aspects of the invention, the methods of the invention can further include administration of a second transcription factor, e.g., Hypoxia-Inducible Factor (HIF)-1α (either full length or a biologically active fragment thereof). Administration of HIF-1α acts synergistically with RTEF-1 to increase angiogenic activity and increases VEGF expression by at least 10%, 20%, 30%, 40%, 50%, 60%, 70%, 80%, 85%, 90%, 95%, 100%, or even more than 100% relative to an untreated control or a control treated only with RTEF-1. When administered with RTEF-1, the RTEF-1/HIF-1α combination increases angiogenesis by at least 10%, 20%, 30%, 40%, 50%, 60%, 70%, 80%, 85%, 90%, 95%, 100%, or even more than 100% above control levels as measured by any method known in the art or described herein. Desirably, the RTEF-1/HIF-1α combination induces collateral blood vessel formation, improves abnormal cardiac function, or increases contractility of heart muscle to a greater extent than does RTEF-1 alone. The HIF-1α is substantially identical (having at least 10%, 20%, 30%, 40%, 50%, 60%, 70%, 80%, 85%, 90%, 95%, 100% sequence identity) to the naturally occurring HIF-1α, such as the human HIF-1α (Accession Numbers NP_851397, NP_001521, and Q16665), mouse HIF-1α (Accession Numbers NP_034561, Q61221, and AAC53461), or bovine HIF-1α (Accession Number Q9XTA5), and includes naturally occurring variants of HIF-1α, such as those containing naturally occurring mutations or polymorphisms. The biological activity of HIF-1α can be determined by assaying for the ability of HIF-1α to promote an increase in the upregulation of VEGF expression (see, e.g., Lee et al., Exp. Mol. Med. 36:1-12, 2004; incorporated herein by reference).

In a preferred embodiment, HIF-1α fragments for use in the invention comprise at least 30 amino acids, preferably 50 amino acids, more preferably 100 amino acids, and most preferably 200 amino acids or more and retain the ability to bind to the VEGF promoter region and upregulate VEGF mRNA or protein levels in the cell or target tissue expressing the HIF-1α fragment.

If desired, the mammal being treated according to this invention may further be provided with a second therapeutic regimen, such as a therapeutic agent (e.g., nitrates, beta-blockers, calcium channel blockers, aspirin, nitroglycerin, chelation therapy, ethylenediaminetetracetric acid, anticoagulants, thrombolytic drugs, and tissue plasminogen activators), surgery (e.g., coronary bypass surgery, vascular surgery, percutaneous transluminal coronary angioplasty, percutaneous transluminal coronary intervention, or organ transplantation), exercise, reduction in smoking, reduction in alcohol intake, low sodium diet, low fat diet, low cholesterol diet, and stress management. The RTEF-1 may be provided with the second therapeutic regimen, the HIF-1α, or both, separately (e.g., within one, two, six, twelve, or twenty hours of each other) or simultaneously (e.g., in the same pharmaceutical formulation).

In another aspect, the invention provides a method of decreasing angiogenesis by administering to the mammal a therapeutically effective amount of a composition that reduces the expression or biological activity of RTEF-1. According to this invention, such a composition decreases VEGF, FGFR, or COX-2 expression by at least 10%, 20%, 30%, 40%, 50%, 60%, 70%, 80%, 85%, 90%, 95%, 100%, or even more than 100% relative to an untreated control. Accordingly, angiogenesis is decreased by at least 10%, 20%, 30%, 40%, 50%, 60%, 70%, 80%, 85%, 90%, 95%, 100%, or even more than 100% relative to an untreated control as measured by any standard method. Using this method, hypervascular conditions, such as cancer (e.g., breast cancer, prostate cancer, brain cancer, pancreatic cancer, lung cancer, stomach cancer, ovarian cancer, cervical cancer, leukemia, lymphoma, and AIDS-related Kaposi's sarcoma), acquired immune deficiency syndrome (AIDS), diabetes, arthritis, psoriasis, and ocular diseases (e.g., macular degeneration and diabetic retinopathy), are treated, reduced, or prevented.

Optionally, the mammal being provided with such treatment may further be provided with a second therapeutic regimen (e.g., chemotherapy, radiotherapy, hormone ablation therapy, anti-inflammatory agents, or steroids). In this respect, the composition of the invention and the second therapeutic regimen may be provided separately (e.g., within one hour, two hours, three hours, six hours, ten hours, or twenty four hours of each other) or simultaneously (e.g., in the same pharmaceutical formulation if the second therapeutic regimen is a therapeutic agent).

In an embodiment of this aspect of the invention, in addition to a composition that reduces the expression or biological activity of RTEF-1, a composition that reduces the expression or biological activity of HIF-1α is also administered. According to this aspect of the invention, the combination of both compositions further decreases VEGF expression by at least 10%, 20%, 30%, 40%, 50%, 60%, 70%, 80%, 85%, 90%, 95%, 100%, or even more than 100% relative to a control that receives only a RTEF-1-directed composition, or an untreated control. Accordingly, angiogenesis is decreased by at least 10%, 20%, 30%, 40%, 50%, 60%, 70%, 80%, 85%, 90%, 95%, 100%, or even more than 100% relative to an untreated control or a control that receives only a RTEF-1-directed composition as measured by any standard method.

In preferred embodiments, a composition that can be used to reduce the mRNA or protein level of RTEF-1 or HIF-1α in a target cell or tissue, or that can be used to reduce the biological activity of RTEF-1 or HIF-1α in a target cell or tissue, include, e.g., a peptide, a polypeptide, a synthetic organic molecule, a naturally occurring organic molecule, a nucleic acid molecule (e.g., a dsRNA for use in RNAi, or an antisense ssRNA), an antibody, or an antigen binding fragment, or a component thereof.

The present invention also provides a method for identifying a candidate compound for treating or reducing hypoxia in a mammal. The method involves the steps of: (a) contacting a sample comprising an RTEF-1 gene (e.g., a sample containing a cell that expresses RTEF-1) with a candidate compound; and (b) measuring RTEF-1 gene expression or RTEF-1 activity. A compound that modulates (e.g., increases) the expression or activity of RTEF-1 relative to such expression or activity in a sample not contacted with the compound (e.g., a sample containing a cell expressing RTEF-1) is identified as a candidate compound for treating or reducing hypoxia in a mammal. In an embodiment of the method, the candidate compound increases angiogenesis in the mammal.

Conversely, the invention also provides a method for identifying a candidate compound for decreasing angiogenesis in a mammal. The method involves the steps of: (a) contacting a sample comprising an RTEF-1 gene (e.g., a cell that expresses RTEF-1) with a candidate compound; and (b) measuring RTEF-1 gene expression or RTEF-1 activity. A compound that alters (e.g., decreases) the level or activity of RTEF-1 relative to such level or activity in a sample not contacted with the compound is identified as a candidate compound for decreasing angiogenesis in a mammal. According to either one of these methods, the cell may endogenously express RTEF-1 or may be genetically altered to express RTEF-1. Optionally, step (b) involves measuring the expression or biological activity of RTEF-1 to assess the stimulatory or inhibitory activity of the candidate compound. In preferred embodiments, the gene of step (a) is an RTEF-1 fusion gene. In other embodiments, step (b) involves the measurement of RTEF-1 mRNA or protein. Preferably, the cell is a mammalian cell (e.g., a human or rodent cell).

The invention further features a method for identifying a candidate compound for treating, preventing, or reducing hypoxia in a mammal. This method involves (a) contacting RTEF-1 protein (e.g., human RTEF-1) with a candidate compound; and (b) determining whether the candidate compound binds the RTEF-1 protein such that a candidate compound that binds the RTEF-1 protein and modulates (e.g., increases) the activity of RTEF-1 is identified as a candidate compound useful for treating or reducing hypoxia. In an embodiment, the candidate compound increases angiogenesis.

Conversely, the method also features a method for identifying a candidate compound for decreasing angiogenesis in a mammal. This method involves (a) contacting an RTEF-1 protein with a candidate compound; and (b) determining whether said candidate compound binds said RTEF-1 protein, such that a candidate compound that binds said RTEF-1 protein and decreases the activity of the RTEF-1 protein is identified as being a candidate compound useful for decreasing angiogenesis.

Any of the candidate compounds identified by the present screening methods may further be tested for their angiogenic activity. In this regard, a compound that increases or decreases angiogenesis by at least 10% relative to a control is identified as a compound useful for increasing or decreasing angiogenesis, respectively. A compound that increases angiogenesis is preferably administered to treat or reduce hypoxia.

In preferred embodiments, the candidate compound is a peptide, a polypeptide, a synthetic organic molecule, a naturally occurring organic molecule, a nucleic acid molecule (e.g., a dsRNA for use in RNAi, or an antisense ssRNA), an antibody, or an antigen binding fragment, or a component thereof.

The invention further provides a kit containing a vector encoding an RTEF-1 protein or an RTEF-1 protein in an amount sufficient to treat or reduce hypoxia as well as instructions for the administration of the RTEF-1 (as a protein or nucleic acid) to a mammal or tissue for treating or reducing hypoxia. In an embodiment, the kit additionally contains a vector encoding a HIF-1α protein or a HIF-1α protein in an amount sufficient to treat or reduce hypoxia in combination with RTEF-1. In an embodiment, the RTEF-1 protein treats or reduces hypoxia by increasing angiogenesis.

Alternatively, the invention also provides a kit containing a composition that reduces the expression or activity of RTEF-1 in an amount sufficient to decrease angiogenesis; and instructions for delivery of said vector to a mammal or tissue for decreasing angiogenesis. In an embodiment, the kit additionally contains a composition that reduces the expression or activity of HIF-1α protein in an amount sufficient to decrease angiogenesis in combination with the RTEF-1-activity decreasing composition. In preferred embodiments, the composition is a compound, such as a peptide, a polypeptide, a synthetic organic molecule, a naturally occurring organic molecule, a nucleic acid molecule (e.g., a dsRNA for use in RNAi, or an antisense ssRNA), an antibody, or an antigen binding fragment, or a component thereof, that reduces the reduces the expression or activity of RTEF-1 (and, optionally, HIF-1α).

By "angiogenesis" is meant the promotion of new blood vessel growth from the existing vasculature. The term also includes "tissue remodeling," which refers to the reformation of the existing vasculature.

By "angiogenic activity" is meant having the ability to increase angiogenesis by at least 10%, 20%, 30%, 40%, 50%, 60%, 70%, 80%, 90%, or more than 100% relative to a control. Angiogenic activity may be determined in vitro by measuring, for example, endothelial cell proliferation, endothelial cell migration, endothelial cell survival, and tubule formation. Alternatively, angiogenic activity may be determined in vivo, by counting or staining vessels, or alternatively, by quantitating functional vessels, using the MATRIGEL® assay, corneal micropocket assay, hind limb ischemic model, and chick chorioallantoic membrane (CAM) assay. Preferably, in vitro assays measure endothelial cell proliferation or survival and preferred in vivo assays are the hind limb ischemic model and the corneal micropocket assay. For the purpose of determining claim scope, the preferred assay is hind limb ischemic model.

By a "candidate compound" is meant a chemical, be it naturally-occurring or artificially-derived. Candidate compounds may include, for example, peptides, polypeptides, synthetic organic molecules, naturally occurring organic molecules, nucleic acid molecules, and components thereof.

By "decreasing angiogenesis" is meant decreasing or reducing vessel growth as measured by any standard method known in the art, as described herein. Preferably, such reduction is at least 10%, 20%, 30%, 40%, 50%, 60%, 70%, 80%, 90%, 95%, 99%, or even more than 100% below control levels. A characteristic decrease conferred by a given compound may be measured using, among others, the assays provided for "angiogenic activity."

By "decreases expression of RTEF-1" or "decreases activity of RTEF-1" is meant to reduce the expression level of RTEF-1 at the mRNA or protein level, or alternatively, to reduce the angiogenic activity of RTEF-1 relative to control conditions. This decrease may be, for example, a decrease of least 0.1-fold, 0.5-fold, 1-fold, 2-fold, 3-fold, 5-fold, 10-fold, 100-fold, or even 1000-fold or greater, relative to control conditions.

By "decreases expression of HIF-1α" or "decreases activity of HIF-1α" is meant to reduce the expression level of HIF-1α at the mRNA or protein level, or alternatively, to reduce the angiogenic activity of HIF-1α relative to control conditions. This decrease may be, for example, a decrease of least 0.1-fold, 0.5-fold, 1-fold, 2-fold, 3-fold, 5-fold, 10-fold, 100-fold, or even 1000-fold or greater, relative to control conditions.

By "dominant negative protein" is meant any polypeptide having at least 50%, 70%, 80%, 90%, 95%, or even 99% sequence identity to 10, 20, 35, 50, 100, 150, or more than 150 amino acids of the wild type protein to which the dominant negative protein corresponds. In addition to inactivating mutations, dominant negative proteins may consist of deletions or truncations of a wild-type molecule. For example, a dominant negative RTEF-1 may be a truncated RTEF-1 mutant that has a deletion such that it no longer functions as a transcriptional activator of VEGF, FGFR, or COX-2.

By "an effective amount" is meant an amount of a compound, alone or in a combination, required to treat, prevent, or reduce a pathological condition characterized by abnormal angiogenesis in a mammal. The effective amount of active compound(s) varies depending upon the route of administration, age, body weight, and general health of the subject. Ultimately, the attending physician or veterinarian will decide the appropriate amount and dosage regimen.

By "high stringency conditions" is meant any set of conditions that are characterized by high temperature and low ionic strength and allow hybridization comparable with those resulting from the use of a DNA probe of at least 40 nucleotides in length, in a buffer containing 0.5 M $NaHPO_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well known by those skilled in the art of molecular biology. See, e.g., F. Ausubel et al., *Current Protocols in Molecular Biology*, John Wiley & Sons, New York, N.Y., 1998, hereby incorporated by reference.

By "hypervascular condition" is meant any pathological condition characterized by an excessive blood flow in a tissue or an abnormal increase in angiogenesis in a tissue relative to a healthy tissue. Although the vascular density in the affected tissues may be comparable to healthy tissues, the angiogenic activity is typically increased. According to this invention, this increase in blood flow or angiogenesis (or angiogenic activity) may be at least 10%, 20%, 30%, 40%, 50%, 60%, 70%, 80%, 90%, 95%, 99%, or even more than 100% above a healthy control tissue. Such conditions include, for example, cancer, diabetes, arthritis, psoriasis, and ocular diseases (e.g., macular degeneration and diabetic retinopathy). In some cases, affected tissues may also contain ischemic regions. In the case of cancer for example, areas characterized by extensive ischemia-induced necrosis are typically surrounded by adjacent cuffs of hypervascularized tissues.

By "ischemic condition" is meant any pathological condition caused by hypoxia or an insufficient blood flow in a tissue. As a result of the scarce oxygen and nutrient supply, the tissue becomes ischemic, and eventually becomes damaged and even necrotic. Such conditions are frequently characterized by the inability of the vascular network to supply oxygen and nutrients to the surrounding tissue and typically have a reduction in the number of functional blood vessels relative to a healthy tissue. According to this invention, such reduction may be at least 10%, 20%, 30%, 40%, 50%, 60%, 70%, 80%, 90%, 95%, 99%, or even more than 100% below a healthy tissue. Ischemic conditions may be associated with injuries to the myocardial tissue, related cardiac tissue, cardiovascular system, tissue (e.g., neurological tissue), or organ (e.g., the brain). Exemplary conditions include angina pectoris, cardiac hypertrophy, myocardial infarct, or congenital heart failure or traumatic brain injury.

By "ischemic tissue" is meant any localized tissue characterized by hypoxia or an inadequate supply of oxygen and nutrients, normally caused by an insufficient inflow of blood (e.g., resulting from a blood vessel obstruction). Tissue ischemia includes pulmonary ischemia, limb ischemia, brain ischemia, retinal ischemia, nerve tissue ischemia, kidney ischemia, skin ischemia, subcutaneous tissue ischemia, ischemia of the gut, and cerebral ischemia. "Peripheral ischemia," as used herein, refers to ischemia found in areas distal to or away from the center of the body, such as the tissue of the limbs. "Myocardial ischemia" refers to inadequate oxygen supply to the myocardium due to circulatory disturbances caused by coronary atherosclerosis, for example. "Brain ischemia" or "ischemia of the brain" refers to a disturbance of the blood supply to an area of the brain. "Retinal ischemia" refers to ischemia found in the retina of the eye. "Nerve tissue ischemia," as used herein, refers to circulatory disturbances found in nerve tissue. "Kidney ischemia" refers to decreased oxygenation and disturbance of blood supply to renal tissues. "Skin ischemia" refers to decreased oxygenation and disturbance of blood supply to the skin. "Subcutaneous tissue ischemia" refers to decreased oxygenation and disturbance of blood supply below the skin. "Ischemia of the gut" refers to ischemia found within the digestive system, including death of part of the intestine following cessation in its blood supply, which often results from narrowing of the supplying artery.

By "increasing angiogenesis" is meant initiating or enhancing the growth of blood vessels. According to this invention, such increase is at least 10%, 20%, 30%, 40%, 50%, 60%, 70%, 80%, 90%, 95%, 99%, or even more than 100% above control levels as measured by any standard method or any method described herein. If the target tissue is not already undergoing angiogenesis, the present method allows the initiation of angiogenesis in the target tissue. However, when the target tissue is already undergoing angiogenesis, the present method provides a means by which the level of angiogenesis is enhanced or heightened.

The term "isolated DNA" is meant DNA that is free of the genes which, in the naturally occurring genome of the organism from which the given DNA is derived, flank the DNA. Thus, the term "isolated DNA" encompasses, for example, cDNA, cloned genomic DNA, and synthetic DNA.

By a "pathological condition characterized by abnormal angiogenesis" is meant any condition characterized by an inadequate supply of oxygen, nutrients, or both to a tissue, be it excessive or insufficient, as compared to a healthy tissue. Such conditions typically result from a disproportioned blood flow in the tissue, whether excessive or insufficient, such that there is an imbalance in the supply and demand of oxygen and nutrients in the tissue. Such conditions include, for example, ischemic conditions, in which there is an overall insufficient blood supply or angiogenesis relative to a healthy tissue. These conditions often result in tissue damage and even necrosis. Pathological conditions of the invention also include hypervascular conditions, in which there is an overall excessive blood supply or angiogenesis relative to a healthy tissue. Although these conditions are not necessarily characterized by an increase in vascular density, there is a net increase in angiogenic activity in affected tissues as compared to healthy tissues that is often associated with an increase in cell proliferation within the tissue. According to this invention, pathological conditions characterized by abnormal angiogenesis are typically treated, reduced, or prevented by reversing the abnormal angiogenesis, either by increasing or decreasing angiogenesis.

By "localized" is meant a selected area of tissue to which therapeutic agents, such as RTEF-1, angiogenic factors, and/or genes encoding such factors, are delivered.

The term "pharmaceutical composition" is meant any composition, which contains at least one therapeutically or biologically active agent and is formulated to be suitable for administration to the patient. Any of these formulations can be prepared by well-known and accepted methods of the art. See, for example, Remington: The Science and Practice of Pharmacy, 20$^{th}$ edition, (ed. A R Gennaro), Mack Publishing Co., Easton, Pa., 2000.

By "small interfering RNAs (siRNAs)" is meant an isolated dsRNA molecule, preferably greater than 10 nucleotides (nt) in length, more preferably greater than 15 nucleotides in length, and most preferably greater than 19 nucleotides in length that is used to identify the target gene or mRNA to be degraded. A range of 19-25 nucleotides is the most preferred size for siRNAs. siRNAs can also include short hairpin RNAs in which both strands of an siRNA duplex are included within a single RNA molecule. siRNA includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides. Such alterations can include the addition of non-nucleotide material, such as to the end(s) of the 21 to 23 nt RNA or internally (at one or more nucleotides of the RNA). In a preferred embodiment, the RNA molecules contain a 3' hydroxyl group. Nucleotides in the RNA molecules of the present invention can also comprise non-standard nucleotides, including non-naturally occurring nucleotides or deoxyribonucleotides. Collectively, all such altered RNAs are referred to as analogs of RNA. siRNAs of the present invention need only be sufficiently similar to natural RNA that it has the ability to mediate RNA interference (RNAi). As used herein, RNAi refers to the ATP-dependent targeted cleavage and degradation of a specific mRNA molecule through the introduction of small interfering RNAs or dsRNAs into a cell or an organism. As used herein "mediate RNAi" refers to the ability to distinguish or identify which RNAs are to be degraded. In preferred embodiments, siRNAs are directed to the RTEF-1 gene (to interfere with transcription) or the RTEF-1 mRNA (to interfere with translation).

As used herein, by "RTEF-1" is meant any polypeptide that exhibits an activity common to its related, naturally occurring RTEF-1 polypeptide (Accession Numbers AAC50763 (SEQ ID NO: 7), Q62296, P48984, or Q62296), preferably in its activated form. Accordingly, the RTEF-1 of the invention is substantially identical to the naturally occurring RTEF-1 (at least 60%, 70%, 80%, 85%, 90%, 95%, or more than 100% identical to the human, mouse, or chick RTEF-1), and when administered, the RTEF-1 has angiogenic activity. Desirably, the RTEF-1 having RTEF-1 biological activity binds the VEGF, FGFR, or COX-2 promoter and induces transcription of the VEGF, FGFR, or COX-2 gene. Preferably, the RTEF-1 increases VEGF, FGFR, or COX-2 transcription by at least 5%, 10%, 20%, 30%, 40%, 50%, 60%, 70%, 80%, 90%, or more than 100% above control levels as measured by any standard method known in the art or described herein. Alternatively, the RTEF-1 of the invention increases angiogenesis by at least 5%, 10%, 20%, 30%, 40%, 50%, 60%, 70%, 80%, 90%, or more than 100% above untreated control levels as measured by any standard method in the art or described herein. RTEF-1 is described, for example, in Stewart et al., (1996) *Genomics* (36): 68-76, U.S. Pat. No. 5,776,776, and Ueyama et al., J. Biol. Chem. 275:17476-17480, 2000, all of which are hereby incorporated by reference. Regions of RTEF-1 that have structural significance for biological function include, e.g., the DNA binding domain at the amino-terminal end of RTEF-1, as is discussed in Ueyama et al., serine residues at the carboxy-terminus of RTEF-1 (e.g., Ser 254, Ser-290, Ser-322, and Ser 358 relative to the human wild-type sequence) the mutation of which has been shown to result in loss of RTEF-1 phosphorylation via interaction with PKC and MAPK and concomitant loss of signaling ability, and the STY domain of RTEF-1 (amino acids 299-358, relative to the human sequence)).

By "RTEF-1 fusion gene" is meant an RTEF-1 promoter and/or all or part of an RTEF-1 coding region operably linked to a second, heterologous nucleic acid sequence. In preferred embodiments, the second, heterologous nucleic acid sequence is a reporter gene, that is, a gene whose expression may be assayed; reporter genes include, without limitation, those encoding glucuronidase (GUS), luciferase, chloramphenicol transacetylase (CAT), green fluorescent protein (GFP), alkaline phosphatase, and β-galactosidase.

By "substantially identical," when referring to a protein or polypeptide, is meant a protein or polypeptide exhibiting at least 75%, but preferably 85%, more preferably 90%, most preferably 95%, or even 99% identity to a reference amino acid sequence. For proteins or polypeptides, the length of comparison sequences will generally be at least 20 amino acids, preferably at least 30 amino acids, more preferably at least 40 amino acids, and most preferably 50 amino acids or the full length protein or polypeptide. Nucleic acids that encode such "substantially identical" proteins or polypeptides constitute an example of "substantially identical"

nucleic acids; it is recognized that the nucleic acids include any sequence, due to the degeneracy of the genetic code, that encodes those proteins or polypeptides. In addition, a "substantially identical" nucleic acid sequence also includes a polynucleotide that hybridizes to a reference nucleic acid molecule under high stringency conditions. Methods to determine identity are available in publicly available computer programs. Computer program methods to determine identity between two sequences include, but are not limited to, the GCG program package (Devereux et al., *Nucleic Acids Research* 12: 387, 1984), BLASTP, BLASTN, and FASTA (Altschul et al., *J. Mol. Biol.* 215:403 (1990). The well-known Smith Waterman algorithm may also be used to determine identity. The BLAST program is publicly available from NCBI and other sources (*BLAST Manual*, Altschul, et al., NCBI NLM NIH, Bethesda, Md. 20894). These software programs match similar sequences by assigning degrees of homology to various substitutions, deletions, and other modifications.

By "therapeutically effective amount," when referring to the treatment, reduction, or prevention of hypoxia or ischemia, is meant an amount of RTEF-1 (nucleic acid or polypeptide) which, when administered to a patient suffering from hypoxia or ischemia, is sufficient to cause a qualitative or quantitative reduction in the symptoms of the hypoxic or ischemic condition. A "therapeutically effective amount," when referring to the treatment, reduction, or prevention of hypoxia or ischemia, can also mean an amount of a candidate compound which, when administered to a patient suffering from hypoxia or ischemia, is sufficient to cause an increase in the expression levels of RTEF-1 such that a concomitant increase in the expression levels of VEGF, FGFR, or COX-2, as measured by the assays described herein, results. When administered before, after, or simultaneously with RTEF-1 (nucleic acid or polypeptide), a therapeutically effective amount of HIF-1α means an amount of HIF-1α (nucleic acid or polypeptide) administered to a patient suffering from hypoxia or ischemia that is sufficient to cause a qualitative or quantitative reduction in the symptoms of the hypoxic or ischemic condition, or an increase in the expression levels of VEGF, as measured by the assays described herein.

"Therapeutically effective amount," when referring to the treatment, reduction, or prevention of a hypervascular condition in a patient, is meant an amount of a candidate compound that is sufficient to cause a qualitative or quantitative reduction in the symptoms of the hypervascular condition. The candidate compound can act by reducing or inhibiting RTEF-1 expression or activity sufficient to cause a qualitative or quantitative reduction in the symptoms of the hypervascular condition. By reducing the expression levels or activity of RTEF-1, administration of a therapeutically effective amount of the candidate compound results in, e.g., a decrease in the expression levels of VEGF, FGFR, or COX-2, as measured by the assays described herein.

By "treating," "reducing," or "preventing" "hypoxia," "an ischemic condition" or "a hypervascular condition" is meant ameliorating such condition before or after it has occurred. As compared with the patient status prior to treatment, such reduction or degree of prevention is at least 5%, 10%, 20%, 40%, 50%, 60%, 80%, 90%, 95%, or 100% as measured by any standard technique. A patient who is being treated for a hypoxic, ischemic condition, or hypervascular condition is one who a medical practitioner has diagnosed as having such a condition. Diagnosis may be by any suitable means known in the art. Methods for diagnosing vascular damage, such as atherosclerosis, by measuring systemic inflammatory markers are described, for example, in U.S. Pat. No. 6,040,147, hereby incorporated by reference. Diagnosis and monitoring may also employ urine tests; microscopic urinalysis; hematocrit; measurements of blood levels of serum potassium, serum creatinine, blood urea nitrogen, fasting glucose, thyroid stimulating hormone, lipid content (HDL, LDL, cholesterol and TG), serum calcium, and serum phosphate, or total cholesterol; electrocardiogram, echocardiogram, white blood cell count, or X-ray. A patient in whom the development of a hypoxic, ischemic, or hypervascular condition is being prevented may or may not have received such a diagnosis. One in the art will understand that these patients may have been subjected to the same standard tests as described above (electrocardiogram, chest X-ray, etc.) or may have been identified, without examination, as one at high risk due to the presence of one or more risk factors (e.g., family history, hypertension, diabetes mellitus, or high cholesterol levels).

The present invention provides significant advantages over standard therapies for the treatment, reduction, or prevention of hypoxic conditions and pathological conditions characterized by abnormal angiogenesis. Hypoxic conditions include, e.g., ischemic conditions that result from a loss of blood flow or due to insufficient angiogenesis. Pathological conditions that can be treated, reduced, or prevented and that involve abnormal angiogenesis include, e.g., hypervascular diseases, such as cancer. Administration of RTEF-1 according to the present invention increases VEGF, FGFR, or COX-2 transcription and causes an increase in angiogenesis and, ultimately, treats, reduces, or prevents a hypoxic or ischemic condition The additional administration of HIF-1α may increase the angiogenic benefits over that observed following the administration of RTEF-1 alone. Conversely, the administration of a pharmaceutical composition that reduces the expression or biological activity of RTEF-1 (optionally in combination with a pharmaceutical composition that reduces the expression or biological activity of HIF-1α) results in a decrease in angiogenesis following the reduction in VEGF, FGFR, or COX-2 transcription, and thereby treats, reduces, or prevents hypervascular conditions. In addition, the candidate compound screening methods provided by this invention allow for the identification of novel therapeutics that modify the injury process, rather than merely mitigating the symptoms.

BRIEF DESCRIPTION OF THE DRAWINGS

FIG. 13 provides the sequence for human RTEF-1 (SEQ ID NO: 7).

DETAILED DESCRIPTION

Figure 1:
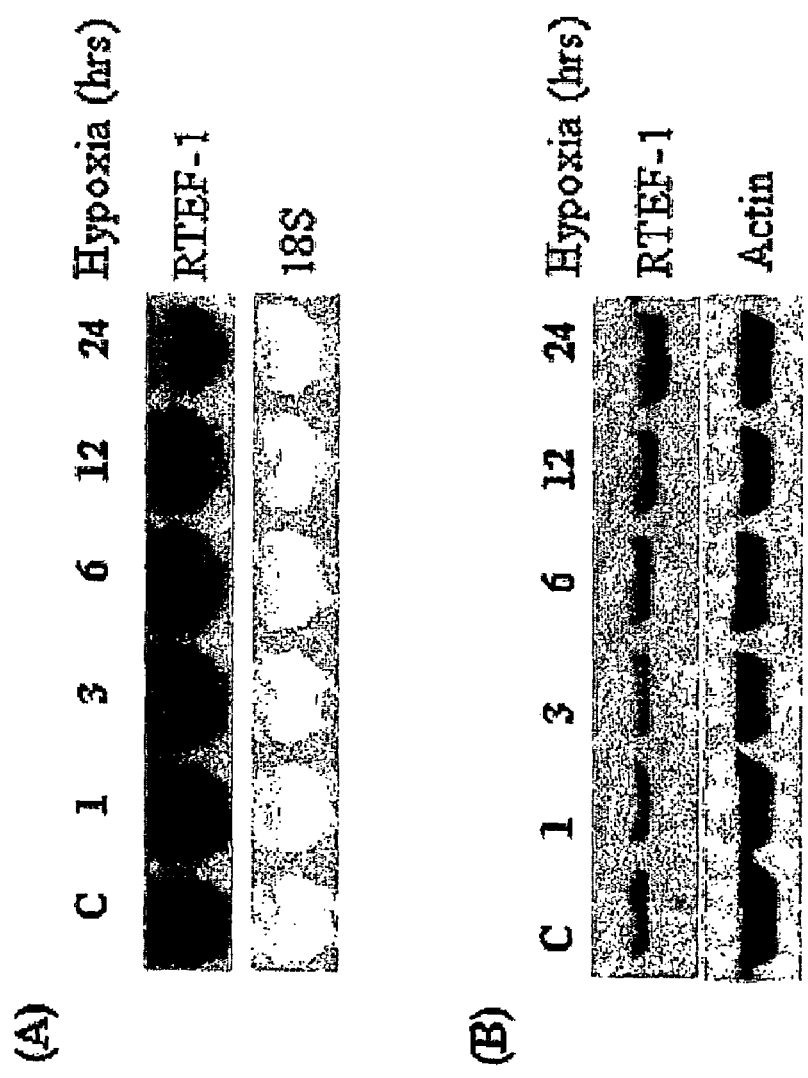
FIG. 1A is a series of photographs showing a Northern blot analysis of a time course of RTEF-1 mRNA expression in bovine aortic endothelial cells (BAEC) cultured in hypoxic conditions.
FIG. 1B is a series of photographs showing RTEF-1 and VEGF protein expression in BAEC cultured under hypoxic conditions. Western blots show that RTEF-1 protein expression increased after 6 h of hypoxic conditions relative to 6 h under normoxic conditions as control. The increase of RTEF-1 expression remains up to 24 h after hypoxia.

The present invention is based on our discovery that Hypoxia-induced Related Transcriptional Enhancer Factor-1 (RTEF-1) induces the expression of VEGF, FGFR, and COX-2, and plays a key role in the growth of new blood vessels and the protection of tissues from ischemia/hypoxia-mediated damage. In particular, we show that RTEF-1 functions as a transcriptional activator of the VEGF, FGFR, and COX-2 genes by binding the VEGF, FGFR, and COX-2 promoters, respectively. Both the FGFR and the VEGF promoter regions contain a Sp1 consensus sequence within the GC-rich area of the promoter that serves as the RTEF-1 binding site. Given that the RTEF-1 binding site within the FGFR and the VEGF promoters is devoid of any M-CAT element, our results are unexpected in view of previous studies reporting the M-CAT element as being the binding sequence for RTEF-1 in muscle cells.

In addition, we show here that RTEF-1 expression is regulated by hypoxia, which has also been shown to drive VEGF, FGFR, and COX-2 expression. Hypoxia regulates various endothelial cell properties and is closely associated with inflammation and angiogenesis. As a result, hypoxia is a central feature of pathological conditions involving abnormal vascularization (e.g., cardiovascular diseases such as myocardial infarction).

We have also determined that the interaction of RTEF-1 with the VEGF promoter is independent of the HIF-1α binding site. This finding is surprising because it implicates RTEF-1 as a novel transcription factor in the regulation of VEGF under hypoxic conditions. Based on our results, RTEF-1-induced expression of VEGF may therefore complement HIF-1α induced VEGF expression.

RTEF-1, in addition to its role in cardiac-gene regulation, may also play a central role in disorders involving abnormal angiogenesis by virtue of its ability to induce VEGF, FGFR, and COX-2 expression in endothelial cells, particularly under hypoxic conditions.

Pathological Disorders

Based on our results, the present invention features methods and compositions useful for the treatment, reduction, and prevention of various pathological conditions characterized by abnormal angiogenesis. Typically, such conditions are associated with an inadequate supply of oxygen, nutrients, or both to a tissue, be it excessive or insufficient. In this regard, the affected tissues experience a disproportionate blood flow, whether in excess or in shortage, such that there is an imbalance in the supply and demand of oxygen and nutrients in the tissue. Alternatively, affected tissues may be associated with a reduced or increased angiogenic activity relative to the corresponding healthy tissue.

These pathological conditions include both ischemic conditions, in which there is an overall insufficient blood supply or angiogenesis, and hypervascular conditions, in which there is an overall excessive blood supply or angiogenesis (or angiogenic activity). According to this invention, these pathological conditions are treated, reduced, or prevented by reversing the abnormal angiogenesis, either by increasing or decreasing angiogenesis. Alternatively, the methods and compositions of the invention can be used to treat or reduce hypoxia-induced cell, tissue, or organ damage by promoting angiogenesis. The methods of the invention can also be used to identify candidate compounds that increase or decrease angiogenesis by increasing or decreasing, respectively, RTEF-1-mediated transactivation of VEGF, FGFR, or COX-2.

Ischemic Conditions

Ischemic conditions can result in extensive tissue damage and necrosis due to an insufficiency in the delivery of nutrients and oxygen to the cells, tissues, or organs of the body and results from an inadequate vascular blood supply. Typically, hypoxia is the driving force underlying such conditions. According to this invention, the reduction in functional blood vessels within the affected tissue may be at least 10%, and even, possibly, more than 100% below a healthy tissue. Ischemic conditions are therefore often associated with injuries to the myocardial tissue, any related cardiac tissue, cardiovascular system, tissue, or organ. Exemplary conditions are described below.

According to this invention, a mammal (e.g., preferably a human) having such a condition is administered with a therapeutically effective amount of RTEF-1. The RTEF-1 preferably has angiogenic activity (i.e. having the ability to increase angiogenesis by at least 10%, but even, possibly, more than 100% relative to a control or the patient prior to therapy, as measured by any standard method or any method described herein) and is at least 10%, preferably at least 80%, or even 100% identical to the sequence of the naturally occurring RTEF-1, including the human, mouse, or chick RTEF-1. As a result of such administration, the expression of VEGF is induced such that the ischemic condition is treated, prevented, or reduced concomitant with an induction in the formation of collateral blood vessel in the tissue affected by or at risk of being affected by ischemia. Typically, the administration of RTEF-1 to the mammal results in an increase in the expression or activity of RTEF-1, or alternatively, in the expression levels of VEGF transcription (as measured by mRNA or protein levels for example) by at least 10%, but possibly even more than 100% above untreated control levels. Alternatively, angiogenesis or the level of tissue vascularization is increased in the localized ischemic area by at least 10%, but possibly even more than 100% above untreated control levels, as measured by any standard technique in the art or those disclosed herein.

Ischemic conditions amenable to treatment according to the present invention include, for example, any disorder characterized by insufficient angiogenesis, such as ischemic heart disease, peripheral vascular disease, myocardial infarction, ischemia-reperfusion, cardioplegia, stroke, ischemic heart disease, coronary atherosclerosis, restenosis after denudation, congestive heart failure, peripheral vascular disease, cerebrovascular disease, ischemic limbs, pulmonary hypertension, endothelial dysfunction, angina pectoris, microvascular angina, arteriosclerosis, arrhythmia, cardiac hypertrophy, renal diseases, a complication of diabetes, restenosis, organ hypertrophies or hyperplasias, septic shock and other inflammatory diseases (e.g., septicemia and endotoxemia), myocardial stunning, and myocardial dysfunction. Thus, the methods of the present invention may be used to reduce myocardial tissue damage (e.g., by substantially preventing tissue damage and inducing tissue protection) in a patient presenting with ongoing ischemic tissue damage (e.g., acute coronary syndromes, such as myocardial infarction or unstable angina), cerebral ischemic damage (e.g., stroke), coronary heart disease (e.g., previous myocardial infarction or unstable angina), or alternatively, a patient who is at high risk for myocardial infarction (eg., exceeding 65 years of age for example and having two or more risk factors for coronary heart disease).

According to this invention, RTEF-1 may be administered as a recombinant polypeptide or as a nucleic acid molecule encoding RTEF-1, either locally or systemically. The RTEF-1 of the invention may further be provided to the mammal as a single or as multiple applications to the target tissue such that the level of vascularization in the target tissue is increased.

The present invention also provides a method for increasing angiogenesis in mammal in need thereof by providing to the mammal a cell, tissue, or organ that contains a therapeutically effective dose of RTEF-1, such that the dose of RTEF-1 provided by the cell, tissue, or organ has a therapeutic or prophylactic effect on the target tissue. In this regard, angiogenesis may be induced by delivering to the ischemic region a cell (e.g. endothelial cell), tissue, or organ that has been genetically engineered to express RTEF-1 either constitutively or in an inducible fashion. By relying on the transplantation of autologous or non-autologous cells that can produce sustained levels of RTEF-1, the need for multiple applications may be circumvented while still maintaining the induction in angiogenesis. As a particular example, cells are isolated from a mammal, cultured, and transfected with expression vectors encoding the RTEF-1 of the invention. Following in vitro manipulations, these cells are injected back into the mammal at the site of tissue ischemia.

If desired, the RTEF-1 of the invention may also be provided to a mammal prophylactically, in situations in which ischemic damage (e.g., surgical procedures) has not yet occurred. The RTEF-1 may therefore be administered to prevent ischemic injury during surgery. Accordingly, the RTEF-1 may be administered prior to, during and/or shortly after cardiac surgery or non-cardiac surgery (e.g., infusion either continuously or in multiple doses over a period of a few days). In this regard, RTEF-1 reduces or prevents future tissue damage (e.g., by preventing tissue damage or by inducing tissue protection) during surgery (e.g., coronary artery bypass grafting surgeries, vascular surgeries, percutaneous transluminal coronary angioplasty or any percutaneous transluminal coronary intervention, organ transplantation, or other non-cardiac surgeries).

Optionally, the RTEF-1 of the invention may be administered in combination with a second therapeutic regimen. For example, RTEF-1 may be administered with or without other angiogenic factors, which at least in combination with the RTEF-1, results in the treatment, prevention, or reduction of a condition characterized by hypoxic damage or insufficient angiogenesis. Such angiogenic factors are described in detail in U.S. Ser. No. 10/293,157 (U.S. Publication Number 20030144200), hereby incorporated by reference. Alternatively, the second therapeutic regimen may be a lifestyle change, including for example, exercise, reduction in smoking, reduction in alcohol intake, low sodium diet, low fat diet, low cholesterol diet, and stress management. These lifestyle changes are particularly important given that the prevention of the cause of ischemia, primarily atherosclerosis, is crucial. The second therapeutic regimen may also be a surgical procedure, such as percutaneous transluminal coronary angioplasty and coronary artery bypass graft surgery, atherectomy, laser angioplasty, carotid endarterectomy surgery. Such procedures are described, for example, in U.S. Ser. No. 10/293, 157, hereby incorporated by reference. Optionally, the second therapeutic regimen may be a therapeutic agent. Exemplary agents include nitrates, beta-blockers, calcium channel blockers, aspirin, nitroglycerin, chelation therapy involving the injection of a cocktail of synthetic amino acid, ethylenediaminetetracetric acid, anticoagulant drugs, thrombolytic drugs, and tissue plasminogen activators. Such therapies are described in detail, for example, in U.S. Pat. Nos. 6,316,419, 6,329,348, and 6,518,255 and U.S. Patent Publication Numbers 20020099029, 20020065240, 20030148968, 20030139333, 20030055021, and 20030143544, all of which are hereby incorporated by reference.

Diagnosis of Ischemia

According to this invention, tissue ischemia may be diagnosed using any standard method known in the art. For example, in myocardial diseases, these methods include a variety of imaging techniques (e.g., radiotracer methodologies such as $^{99}$mTc-sestamibi scanning, x-ray, and MRI scanning) and physiological tests.

For example, diagnostic tests employed to detect myocardial ischemia include resting, exercise, or ambulatory electrocardiograms; scintigraphic studies (radioactive heart scans); echocardiography; coronary angiography; and positron emission tomography. Diagnostic tests for transient ischemic attacks (TIA) include physician assessment of symptoms, computed tomography scans (CT scans), carotid artery ultrasound (Doppler ultrasonography), and magnetic resonance imaging. Angiography may also be used to detect ischemia of any organ.

An electrocardiogram (ECG) may similarly show cardiac activity and may therefore reveal a lack of oxygen. In this regard, approximately 25% of patients with angina have normal electrocardiograms. Another type of electrocardiogram, the exercise stress test, measures response to exertion when the patient is exercising on a treadmill or a stationary bike. Alternatively, ischemia may be diagnosed by means of an ambulatory ECG, in which the patient is monitored with a Holter monitor for 12, 24, or 48 hours.

Optionally, myocardial perfusion scintigraphy and radionuclide angiography may also be employed. Such procedures involve the injection of a radioactive material (e.g., thallium), which is in turn absorbed by healthy tissues. A gamma scintillation camera displays and records a series of images of the radioactive material's movement through the heart. A perfusion scan is sometimes performed at the end of a stress test.

Alternatively, echocardiograms may be used to detect ischemic damage. In this regard, sound waves are used to create an image of the heart's chambers and valves and can reveal abnormalities in the heart wall that indicate ischemia; however, coronary arteries are not assessed directly.

Coronary angiography may also be used because of its accuracy as a diagnostic technique. This technique shows the heart's chambers, great vessels, and coronary arteries by using a contrast solution and X-ray technology. A moving picture is recorded of the blood flow through the coronary arteries.

Positron emission tomography (PET) is a non-invasive nuclear test used to evaluate the heart tissue and may be used according to the present invention. A PET scanner traces high-energy gamma rays released from radioactive particles to provide three-dimensional images of the heart tissue. In addition, computed tomography scans (CT scans) and magnetic resonance imaging SRI), which are computerized scanning methods, may further be employed. CT scanning uses a thin x-ray beam to show three-dimensional views of soft tissues. MRI uses a magnetic field to produce clear, cross-sectional images of soft tissues.

With regards to cerebrovascular damage, scans of the brain may be performed to confirm a diagnosis of stroke and to determine the type of stroke. This is particularly important given that the treatment of different types of stroke may differ. These tests include: computed tomography scan (CT scan), magnetic resonance imaging (I, transcranial doppler (TCD) imaging, and SPECT imaging.

Administration of RTEF-1

As previously stated, the induction of angiogenesis according to the present invention, involves the administration of RTEF-1 to a mammal resulting in an induction in VEGF, FGFR, or COX-2 levels, which is followed by an increase in angiogenesis. The mammal being treated may be provided with RTEF-1 as a recombinant polypeptide (e.g., by microinjection), or alternatively, as a nucleic acid (e.g., a plasmid vector or a viral vector) encoding RTEF-1. The mammal may be administered with the RTEF-1 either locally (within or adjacent to the ischemic or hypoxic tissues) or systemically. Optionally, the mammal may be provided with a cell, tissue, or organ expressing RTEF-1. Such cells, tissues, or organs may have been provided with the RTEF-1 of the invention.

General techniques for the delivery of nucleic acid to endothelial cells can be used in the present invention for the delivery of nucleic acids encoding, e.g., RTEF-1. These general techniques are described in U.S. Pat. Nos. 5,830,879 and 6,258,787 and are incorporated herein by reference. In the present invention the nucleic acid may be any nucleic acid (DNA or RNA) including genomic DNA, cDNA, and mRNA, encoding RTEF-1. The nucleic acid encoding the desired protein may be obtained using routine procedures in the art, e.g. recombinant DNA, PCR amplification.

Administration of the RTEF-1 to the target tissue can be accomplished either in vivo or ex vivo. Therefore, for example, the target tissue can be removed from the mammal of the present invention, provided with the RTEF-1, and then reimplanted into the mammal. Ex vivo administration of the RTEF-1 to the target tissue helps to minimize undesirable induction of angiogenesis in non-targeted tissue.

An expression vector of this invention may be in any of several forms, including, but not limited to, RNA, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, complexed with compounds such as PEG to immunologically "mask" the molecule and/or increase half-life, or conjugated to a non-viral protein. Preferably, the polynucleotide is DNA and includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. Typically, plasmids encoding the RTEF-1 are administered to a mammal in an amount of about 1 nanogram to about 5000 micrograms of DNA. Desirably, compositions contain about 5 nanograms to 1000 micrograms of DNA, 10 nanograms to 800 micrograms of DNA, 0.1 micrograms to 500 micrograms of DNA, 1 microgram to 350 micrograms of DNA, 25 micrograms to 250 micrograms of DNA, or 100 micrograms to 200 micrograms of DNA. Alternatively, administration of recombinant adenoviral vectors encoding the RTEF-1 into a mammal may be administered at a concentration of at least $10^5$, $10^6$, $10^7$, $10^8$, $10^9$, $10^{10}$, or $10^{11}$ plaque forming unit (pfu).

Furthermore, the viral vector's coat protein can be modified so as to incorporate a specific protein binding sequence, as described in U.S. Pat. No. 5,432,075, or the viral vector's coat protein can be modified so as to decrease the viral vector's ability or inability to be recognized by a neutralizing antibody directed against the wild-type coat protein, as described in International Patent Application WO 98/40509.

Alternatively, the RTEF-1 of the invention may be administered to the mammal as a recombinant polypeptide having an amino acid sequence substantially identical to the naturally occurring RTEF-1 (e.g., human, mouse, or chick). The RTEF-1 is therefore a polypeptide exhibiting at least 75%, but preferably 80%, more preferably 90%, most preferably 95%, or even 99% identity to a reference amino acid sequence of the naturally occurring RTEF-1. The length of comparison sequences will generally be at least 20 amino acids, preferably at least 30 amino acids, more preferably at least 40 amino acids, and most preferably 50 amino acids or the fall-length. The RTEF-1 protein may be directly administered to ischemic tissue of a mammal by any standard technique, using for example microinjection techniques. Alternatively, the RTEF-1 protein may be administered systematically by any standard route.

Overall, the pharmaceutical composition including the RTEF-1 of the invention can be provided by injection (e.g., intramuscular, intranasal, intraperitoneal, intradermal, subcutaneous, intravenous, intraarterial, or intraocular), as well as by oral, topical (e.g., ointment, or patch), or transdermal administration. Alternatively, these compositions may be provided by inhalation, or by suppository. Compositions according to the invention may also be provided to mucosal tissue, by lavage to vaginal, rectal, urethral, buccal, and sublingual tissue for example.

It is understood that a biological effect may require multiple administration of the RTEF-1. While administration of a dose of the angiogenic vector can be accomplished through a single application (e.g., a single injection or a single topical application) to the target tissue, preferably, administration of the dose is via multiple applications of the angiogenic vector. The multiple applications can be 2, 3, 4, 5, or more applications, preferably 5 or more applications, more preferably 8 or more applications, and most preferably at least 10 (e.g., 10, 15, or 20) applications. Multiple applications provide an advantage over single applications in that they can be manipulated by such parameters as a specific geometry defined by the location on the target tissue where each application is administered. The administration of a single dose of the angiogenic vector via multiple applications can be better controlled, and the effectiveness with which any given dose is administered can be maximized. In this way, the undesirable effects associated with administration of a single point application of a large dose can be minimized.

The pharmaceutical compositions according to the present invention are formulated according to the mode of administration to be used. In cases where pharmaceutical compositions are injectable pharmaceutical compositions, they are sterile, pyrogen-free and particulate free. An isotonic formulation is preferably used. Generally, additives for isotonicity can include for example sodium chloride, dextrose, mannitol, sorbitol and lactose. Stabilizers may also be used and include, for example, gelatin and albumin.

Modes for Delivering Nucleic Acids

For any of the nucleic acid applications described herein, standard methods for administering nucleic acids can be used. For example, to simplify the manipulation and handling of the nucleic acid encoding, e.g., the RTEF-1 protein, the nucleic acid is preferably inserted into a cassette where it is operably linked to a promoter (see below). The promoter must be capable of driving expression of the RTEF-1 protein in the desired target host cell. The selection of appropriate promoters can readily be accomplished. Preferably, one would use a high expression promoter. Other elements that can enhance expression can also be included (e.g., enhancers or a system that results in high levels of expression such as a tat gene and tar element). The recombinant vector can be a plasmid vector such as pUC118, pBR322, or other known plasmid vectors, that includes, for example, an E. coli origin of replication (see, Sambrook, et al., Molecular Cloning: A Laboratory Manual, Cold Spring Harbor Laboratory press, 1989). The plasmid vector may also include a selectable marker such as the β lactamase gene for ampicillin resistance, provided that the marker polypeptide does not adversely affect the metabolism of the organism being treated. The cassette can also be bound to a nucleic acid binding moiety in a synthetic delivery system, such as the system disclosed in PCT Publication No. WO95/22618. The nucleic acid can be introduced into the cells by any means appropriate for the vector employed. Many such methods are well known in the art (Sambrook et al., supra, and Watson et al., "Recombinant DNA", Chapter 12, 2d edition, Scientific American Books, 1992). Recombinant vectors can be transferred by methods such as calcium phosphate precipitation, electroporation, liposome-mediated transfection, gene gun, microinjection, viral capsid-mediated transfer, polybrene-mediated transfer, or protoplast fusion. For a review of the procedures for liposome preparation, targeting and delivery of contents, see Mannino and Gould-Fogerite, (Bio Techniques, 6:682-690, 1988), Felgner and Hohm, (Bethesda Res. Lab. Focus, 11:21, 1989) and Maurer (Bethesda Res. Lab. Focus, 11:25, 1989).

Transfer of the recombinant vector (either plasmid vector or viral vectors) can be accomplished through direct injection, e.g., via intravenous delivery. Gene delivery using adenoviral vectors or adeno-associated vectors (AAV) can also be used. Adenoviruses are present in a large number of animal species, are not very pathogenic, and can replicate equally well in dividing and quiescent cells. As a general rule, adenoviruses used for gene delivery are lacking one or more genes required for viral replication. Replication-defective recombinant adenoviral vectors used for the delivery of a RTEF-1 protein, can be produced in accordance with art-known techniques (see Quantin et al., Proc. Natl. Acad. Sci. USA, 89:2581-2584, 1992; Stratford-Perricadet et al., J. Clin. Invest., 90:626-630, 1992; and Rosenfeld et al., Cell, 68:143-155, 1992).

Once transferred, the nucleic acid is expressed by the cells at the site of hypoxia or injury for a period of time sufficient to increase the expression levels of RTEF-1 protein, such that treatment, reduction, or prevention of the hypoxic condition results. Because the vectors containing the nucleic acid are not normally incorporated into the genome of the cells, expression of the protein of interest takes place for only a limited time. Typically, the protein is expressed at therapeutic levels for about two days to several weeks, preferably for about one to two weeks. Re-application of the DNA can be utilized to provide additional periods of expression of the therapeutic protein.

Hypervascular Conditions

A hypervascular condition, according to the present invention, is any pathological condition characterized by an excessive blood flow in a tissue or an abnormal increase in angiogenesis in the tissue relative to a healthy tissue. According to this invention, this increase in blood flow or angiogenesis may be at least 10%, but possibly even more than 100% above a healthy control tissue.

Accordingly, further provided in this invention are methods for reducing angiogenesis in a mammal by administering to the mammal a composition that reduces the expression or activity of RTEF-1 such that VEGF, FGFR, or COX-2 expression is reduced, in turn decreasing angiogenesis in a target tissue. This invention is therefore useful for treating, reducing, or preventing disorders characterized by an abnormal increase in angiogenesis. Such disorders include, for example, cancer (e.g., breast cancer, prostate cancer, brain cancer, pancreatic cancer, lung cancer, stomach cancer, ovarian cancer, cervical cancer, leukemia, lymphoma, and AIDS-related Kaposi's sarcoma), psoriasis, arthritis, diabetes, AIDS, and ocular diseases (e.g., macular degeneration and diabetic retinopathy).

According to the present invention, an inhibitor of RTEF-1 is any agent having the ability to reduce the production or the activity of RTEF-1 by at least 10%, but possibly even 100% or more relative to an untreated control cell as determined by any standard method in the art, including those described herein. The RTEF-1 inhibitor may also inhibit VEGF transcription by at least 10%, but possibly 100% or more relative to an untreated control cell as determined by any standard method in the art, including those described herein. Alternatively, the inhibitor may treat, prevent, or reduce a hypervascular condition when administered to a mammal by at least 10%, %, but possibly even 100% or more relative to an untreated control. Such reduction or prevention in angiogenesis may be measured by any technique known in the art such as those described herein. Exemplary compounds that may be used according to this invention include any of the compounds identified using the screening methods of the invention.

Optionally, the RTEF-1 inhibitor may be a small molecule antagonist or an antisense to RTEF-1. By binding to the complementary nucleic acid sequence (the sense or coding strand), antisense nucleobase oligomers are able to inhibit protein expression presumably through the enzymatic cleavage of the RNA strand by RNAse H. Preferably the antisense nucleobase oligomer is capable of reducing RTEF-1 protein expression in a cell that expresses RTEF-1. Preferably the decrease in RTEF-1 protein expression is at least 10% relative to cells treated with a control oligonucleotide, more preferably 25%, and most preferably 50% or greater. Methods for selecting and preparing antisense nucleobase oligomers are well known in the art. For an example of the use of antisense nucleobase oligomers to downregulate VEGF expression, see U.S. Pat. No. 6,410,322, incorporated herein by reference. Methods for assaying levels of protein expression are also well known in the art and include western blotting, immunoprecipitation, and ELISA.

RNA interference (RNAi) may also be used to target the RTEF-1 as it provides a powerful method of gene silencing in eukaryotic cells, including mammalian cells, such as the vascular endothelial cells of the present invention. RNA interference has previously been described (O'Neil N J, et al., *Am J Pharmacogenomics* (2001): 45-53). The basic technique of RNAi involves introducing a sequence-specific double-stranded RNA into the cell, in which the double-stranded RNA (dsRNA) corresponds to a gene or mRNA of interest. The dsRNA causes the degradation of the corresponding mRNA. In the RNAi reaction, both the sense and anti-sense strands of a dsRNA molecule are processed into small RNA fragments or segments ranging in length from 21 to 23 nucleotides (nt) and having 2-nucleotide 3' tails. Alternatively, synthetic dsRNAs, which are 21 to 23 nt in length and have 2-nucleotide 3' tails, can be synthesized, purified and used in the reaction. These 21 to 23 nt dsRNAs are known as "guide RNAs" or "short interfering RNAs" (siRNAs).

The siRNA duplexes then bind to a nuclease complex composed of proteins that target and destroy endogenous mRNAs having homology to the siRNA within the complex. Although the identity of the proteins within the complex remains unclear, the function of the complex is to target the homologous mRNA molecule through base pairing interactions between one of the siRNA strands and the endogenous mRNA. The mRNA is then cleaved approximately 12 nt from the 3' terminus of the siRNA and degraded. In this manner, specific genes can be targeted and degraded, thereby resulting in a loss of protein expression from the targeted gene. siRNAs can also be chemically synthesized or obtained from a company that chemically synthesizes siRNAs (e.g., Dharmacon Research Inc., Pharmacia, or ABI).

The specific requirements and modifications of dsRNA are described in PCT Publication No. WO01/75164 (incorporated herein by reference). While dsRNA molecules can vary in length, it is most preferable to use siRNA molecules which are 21- to 23-nucleotide dsRNAs with characteristic 2- to 3-nucleotide 3' overhanging ends typically either (2'-deoxy) thymidine or uracil. The siRNAs typically comprise a 3' hydroxyl group. Single stranded siRNA as well as blunt ended forms of dsRNA can also be used. In order to further enhance the stability of the RNA, the 3' overhangs can be stabilized against degradation. In one such embodiment, the RNA is stabilized by including purine nucleotides, such as adenosine or guanosine. Alternatively, substitution of pyrimidine nucleotides by modified analogs, e.g., substitution of uridine 2-nucleotide overhangs by (2'-deoxy)thymide is tolerated and does not affect the efficiency of RNAi. The absence of a 2' hydroxyl group significantly enhances the nuclease resistance of the overhang in tissue culture medium.

Alternatively, siRNA can be prepared using any of the methods set forth in PCT Publication No. WO0175164 (incorporated herein by reference) or using standard procedures for in vitro transcription of RNA and dsRNA annealing procedures as described in Elbashir et al. (Genes & Dev., 15:188-200, 2001). siRNAs are also obtained as described in Elbashir et al. by incubation of dsRNA that corresponds to a sequence of the target gene in a cell-free Drosophila lysate from syncytial blastoderm Drosophila embryos under conditions in which the dsRNA is processed to generate siRNAs of about 21 to about 23 nucleotides, which are then isolated using techniques known to those of skill in the art. For example, gel electrophoresis can be used to separate the 21-23 nt RNAs and the RNAs can then be eluted from the gel slices. In addition, chromatography (e.g., size exclusion chromatography), glycerol gradient centrifugation, and affinity purification with antibody can be used to isolate the 21 to 23 nt RNAs.

A variety of methods are available for transfection, or introduction, of dsRNA or oligonucleotides into mammalian cells. For example, there are several commercially available transfection reagents including but not limited to: TransIT-TKO™ (Mirus, Cat. #MIR 2150), Transmessenger™ (Qiagen, Cat. #301525), and Oligofectamine™ (Invitrogen, Cat. #MIR 12252-011). Protocols for each transfection reagent are available from the manufacturer.

In the present invention, the dsRNA, or siRNA, is complementary to the mRNA sequence of RTEF-1 mRNA and can reduce or inhibit expression of RTEF-1. Preferably, the decrease in RTEF-1 protein expression is at least 10% relative to cells treated with a control dsRNA or siRNA, more preferably 25%, and most preferably at least 50%. Methods for assaying levels of protein expression are also well known in the art and include western blotting, immunoprecipitation, and ELISA.

In the present invention, the nucleic acids used include any modification that enhances the stability or function of the nucleic acid in any way. Examples include modifications to the phosphate backbone, the internucleotide linkage, or to the sugar moiety.

Alternatively, the RTEF-1 inhibitor agent may be a dominant negative protein or a nucleic acid encoding a dominant negative protein that interferes with the biological activity of RTEF-1. A dominant negative protein is any amino acid molecule having a sequence that has at least 50%, 70%, 80%, 90%, 95%, or even 99% sequence identity to at least 10, 20, 35, 50, 100, or more than 150 amino acids of the wild type protein to which the dominant negative protein corresponds. For example, a dominant-negative RTEF-1 protein may have mutation such that it no longer functions as a VEGF, FGFR, or COX-2 transcriptional activator.

According to this invention, the dominant negative protein may be administered as an expression vector. The expression vector may be a non-viral vector or a viral vector (e.g., retrovirus, recombinant adeno-associated virus, or a recombinant adenoviral vector). Alternatively, the dominant negative protein may be directly administered as a recombinant protein to the dorsal root ganglia using, for example, microinjection techniques.

If desired, the mammal being treated may also be provided a second therapeutic regimen in addition to the treatment of the invention. Such regimens may include any standard therapy typically employed to treat the condition being treated, including for example, chemotherapy, radiotherapy, hormone ablation therapy, anti-inflammatory agents, or steroids. The methods of the present invention may also be provided with regimens that are used to treat, prevent, or reduce conditions in which a reduction in angiogenesis is desired (e.g., cancer, arthritis, psoriasis, and macular degeneration).

Tissue-Specific Promoters

According to this invention, the therapeutic composition of the invention (the RTEF-1 or the RTEF-1 inhibitor) may be targeted to a specific tissue within the mammal being treated. Such a strategy may be particularly useful in situations in which the systemic administration of angiogenic peptides, such as VEGF protein, can lead to the promiscuous induction of angiogenesis, which may cause blindness and increase the aggressiveness of tumor cells, for example. In order to attenuate or prevent such negative side-effects, it may be desirable to induce or reduce angiogenesis only in the tissue which requires it (i.e., the target tissue). The present invention therefore provides methods for cell targeting not only by delivery of the transgene into the coronary artery, or femoral artery, or other localized sites for example, but also the use of tissue-specific promoters. Any tissue-specific promoter known in the art may be used according to the invention.

By fusing, for example, tissue-specific transcriptional control sequences of left ventricular myosin light chain-2 ($MLC_{2v}$) or myosin heavy chain (MHC) to a transgene within the adenoviral construct, transgene expression is limited to ventricular cardiac myocytes. Cardiac-specific expression has been reported previously by Lee, et al. (*J. Biol. Chem.*, 267:15875-15885, 1992). The $MLC_{2v}$ promoter contains 250 bp, and fits easily within the adenoviral-5 packaging constraints. The myosin heavy chain promoter, known to be a vigorous promoter of transcription, provides a reasonable alternative cardiac-specific promoter and contains less than 300 bp. Other promoters, such as the troponin-C promoter, while highly efficacious and sufficiently small, is less tissue specific. By using the $MLC_{2v}$ or MHC promoters and delivering the transgene in vivo, it is believed that the cardiac myocyte alone (that is without concomitant expression in endothelial cells, smooth muscle cells, and fibroblasts within the heart) will provide adequate expression of the angiogenic or antiangiogenic protein to promote or reduce angiogenesis, respectively. Limiting expression to the cardiac myocyte may further avoid the potentially harmful effect of angiogenesis in non-cardiac tissues such as the retina. Endothelial-specific promoters have also been previously described (Lee, et al., *J. Biol. Chem.*, 265:10446-10450, 1990).

Target Tissues

Any suitable tissue can be subject to administration within the context of the present invention. Preferably, the target tissue comprises receptors capable of binding VEGF or COX-2, or tissue capable of responding to FGF. Most preferably, the target tissue comprises endothelial cells. Generally, the target tissue will be a part of or form a discrete organ, e.g., a muscle, such as the heart.

Generally, the source and/or target locations may be any tissue(s) that is a part of, or forms, a discrete organ, e.g., a muscle, such as the heart. The source location preferably is an angiogenically functional location, e.g., a location in the host that has a sufficient level of perfusion of blood, such as an area near existing blood vessels (preferably with a significant amount of existing blood vessels). The target location preferably is an actual or potential angiogenically dysfunctional location, such as a location in the host that is either undergoing or is at risk of undergoing ischemia or any other condition in which the growth of new, or extension of existing, blood vessels is desirable.

Typically, the target tissue will be suffering from or be at risk of suffering from ischemic damage which results when the tissue is deprived of an adequate supply of oxygenated blood. The interruption of the supply of oxygenated blood is often caused by a vascular occlusion. Such vascular occlusion can be caused by arteriosclerosis, trauma, surgical procedures, disease, and/or other indications. There are many ways to determine if a tissue is at risk of suffering ischemic damage from undesirable vascular occlusions. Such methods are described above.

For example, the blood supply to discrete organs such as the brain, heart, pancreas, entire limbs, or generalized areas of the body, such as a foot, can be attenuated by disease, trauma, surgery, or other events. Additionally, the planning of a surgical procedure can be predictive of the interruption of blood supply through a particular portion of a patient's vasculature. Prior treatment according to the present method can substantially improve the desired outcome of these surgeries. In that case, treatment preferably occurs about one day to about six weeks before said surgery, and more preferably about two to about fourteen days, even more preferably three days prior to surgery.

Alternatively, the target location may be any angiogenically dysfunctional location in which the regression of blood vessels is desired. Preferably, these locations are dependent on VEGF, FGFR, or COX-2, such that the administration of a RTEF-1 inhibitor results in a downregulation of VEGF, FGFR, or COX-2, followed by a reduction in angiogenesis. In this regard, the RTEF-1 inhibitor may be injected, e.g., intratumorally, or may be applied topically, e.g., in the case of psoriatic lesions.

Dosage

The desired dosage (i.e., total dosage to the host) is such that angiogenesis is induced in the target location, e.g., such that there is a therapeutic and/or prophylactic effect on target location. Desirably, the dosage is such that induction of angiogenesis in non-targeted tissue is minimized. The dosage also will vary depending upon the angiogenic mediator to be administered.

Methods to Measure Angiogenesis

According to this invention, angiogenesis may be detected and quantitated using any standard technique known in the art. Such techniques are described, for example, in U.S. Ser. No. 10/198,917 (U.S. Patent Publication Number 20030139333), hereby incorporated by reference. Such techniques include in vitro assays, such as assays measuring the biological function of endothelial cells (e.g., EC migration, EC proliferation, EC survival, and tubule formation) and in vivo assays, by counting or staining for vessels, or alternatively, by measuring the number of functional vessels, using a MATRIGEL® assay, corneal micropocket assay, hind limb ischemic model, and chick chorioallantoic membrane (CAM) assay.

Screening Assays

The present invention provides screening methods to identify compounds that can increase or decrease angiogenesis. Useful angiogenic-inducing compounds include any agent that can increase the expression or biological activity of RTEF-1 or VEGF, FGFR, or COX-2. Useful antiangiogenic compounds include any agent that can decrease the expression or biological activity of RTEF-1 or VEGF, FGFR, or COX-2. The method of screening may involve high-throughput techniques.

A number of methods are available for carrying out such screening assays. According to one approach, candidate compounds are added at varying concentrations to the culture medium of cells expressing RTEF-1. Gene expression is then measured, for example, by standard Northern blot analysis (Ausubel et al., supra), using any appropriate fragment prepared from the nucleic acid molecule of RTEF-1 as a hybridization probe. The level of gene expression in the presence of the candidate compound is compared to the level measured in a control culture medium lacking the candidate molecule. If desired, the effect of candidate compounds may, in the alternative, be measured at the level of polypeptide production using the same general approach and standard immunological techniques, such as Western blotting or immunoprecipitation with an antibody specific for RTEF-1 or VEGF, FGFR, or COX-2. For example, immunoassays may be used to detect or monitor the expression of RTEF-1 or VEGF, FGFR, or COX-2. Polyclonal or monoclonal antibodies which are capable of binding to such a polypeptide may be used in any standard immunoassay format (e.g., ELISA, Western blot, or RIA assay) to measure the level of RTEF-1 or VEGF, FGFR, or COX-2.

Alternatively, the screening methods of the invention may be used to identify candidate compounds that increase or decrease the transcriptional activity of RTEF-1 using any standard assay known in the art. For example, a candidate compound may be tested for its ability to increase or decrease the transcription activity of RTEF-1 as described further below.

As a specific example, mammalian cells (e.g., rodent cells) that express a nucleic acid encoding RTEF-1 are cultured in the presence of a candidate compound (e.g., a peptide, polypeptide, synthetic organic molecule, naturally occurring organic molecule, nucleic acid molecule, or component thereof). Cells may either endogenously express the RTEF-1 or may alternatively, be genetically engineered by any standard technique known in the art (e.g., transfection and viral infection) to overexpress RTEF-1. The expression of RTEF-1 is measured in these cells by means of Western blot analysis and subsequently compared to the level of expression of the same protein in control cells that have not been contacted by the candidate compound. A compound which promotes an increase or decrease in the expression of RTEF-1 is considered useful in the invention. Given its ability to increase or decrease the expression of RTEF-1, such a molecule may be used, for example, as an angiogenic or antiangiogenic therapeutic agent to treat, reduce, or prevent ischemic or hypervascular conditions, respectively.

Alternatively, or in addition, candidate compounds may be screened for those which specifically bind to and inhibit RTEF-1. The efficacy of such a candidate compound is dependent upon its ability to interact with RTEF-1. Such an interaction can be readily assayed using any number of standard binding techniques and functional assays (e.g., those described in Ausubel et al., supra). For example, a candidate compound may be tested in vitro for interaction and binding with RTEF-1 and its ability to modulate angiogenesis may be assayed by any standard assays (e.g., those described herein).

In one particular example, a candidate compound that binds to RTEF-1 may be identified using a chromatography-based technique. For example, a recombinant RTEF-1 protein may be purified by standard techniques from cells engineered to express the RTEF-1 (e.g., those described above) and may be immobilized on a column. A solution of candidate compounds is then passed through the column, and a compound specific for RTEF-1 is identified on the basis of its ability to bind to RTEF-1 and be immobilized on the column. To isolate the compound, the column is washed to remove non-specifically bound molecules, and the compound of interest is then released from the column and collected. Compounds isolated by this method (or any other appropriate method) may, if desired, be further purified (e.g., by high performance liquid chromatography).

In addition, these candidate compounds may be tested for their ability to function as angiogenic or antiogenic agents using any method known in the art or any method described herein. Compounds isolated by this approach may be used, for example, as therapeutics to treat, reduce, or prevent ischemic or hypervascular conditions. Compounds which are identified as binding to RTEF-1 with an affinity constant less than or equal to 10 mM are considered particularly useful in the invention.

Ultimately, the angiogenic or antiangiogenic efficacy of any of the candidate compounds identified by the present screening methods may be tested using any of the angiogenesis assays described above.

Potential antiangiogenic and angiogenic agents include organic molecules, peptides, peptide mimetics, and polypeptides. Antiangiogenic agents also include antibodies that bind to a nucleic acid sequence or polypeptide that encodes RTEF-1 and thereby inhibit or extinguish their activity. Potential antiangiogenic agents also include small molecules that bind to and occupy the binding site of RTEF-1 thereby preventing binding to cellular binding molecules, such that normal biological activity is prevented. Other potential antiangiogenic agents include antisense molecules.

Furthermore, each of the compounds identified by the present screening methods may also be used as lead compounds in the discovery and development of angiogenic or antiangiogenic compounds.

Test Compounds and Extracts

In general, compounds capable of inducing analgesia are identified from large libraries of both natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their analgesic activity should be employed whenever possible.

When a crude extract is found to have an analgesic activity, or a binding activity, further fractionation of the positive lead extract is necessary to isolate chemical constituents responsible for the observed effect. Thus, the goal of the extraction, fractionation, and purification process is the careful characterization and identification of a chemical entity within the crude extract having analgesic activity. Methods of fractionation and purification of such heterogenous extracts are known in the art. If desired, compounds shown to be useful agents for the treatment of pain are chemically modified according to methods known in the art.

The results of the invention are now described in more detail in the following examples. These examples are provided to illustrate the invention and should not be construed as limiting.

Example 1

RTEF-1 is Inducible in Response to Hypoxia

Based on results we obtained from DNA microarray experiments, we found that the expression of RTEF-1 is increased three times in endothelial cells cultured under hypoxic conditions. To confirm this observation, we next performed Northern blot analysis to measure the time-dependent level of RTEF-1 mRNA isolated from total RNA derived from bovine aortic endothelial cells (BAEC) cultured in hypoxia (<1% $O_2$). FIGS. 1A and 1B show that RTEF-1 is induced by hypoxia and that such expression peaked about 6 hours following exposure to hypoxia.

To further understand the function of RTEF-1 under hypoxic conditions and to determine the target genes of RTEF-1 in endothelial cells, RTEF-1 was overexpressed in BAEC cells by transfection of RTEF-1 cDNA. VEGF was identified as a protein that was upregulated in BAEC cells transfected with and overexpressing RTEF-1 (FIG. 2A). VEGF expression was further increased under hypoxic conditions in the presence of overexpressed RTEF-1 (FIG. 2B). In this regard, the expression of VEGF was not only induced by hypoxia but was further enhanced by RTEF-1.

Based on the above data, we proposed that RTEF-1 may play a role in promoting the expression of VEGF by regulating its promoter activity, particularly in hypoxic conditions.

Example 2

VEGF is a Potential Target Gene for RTEF-1

Previous reports have suggested that RTEF-1 transcriptional regulation is mediated through the M-CAT element which contains the following consensus sequence: CATN(T/C)(T/C)(Farrance et al., (1992) *J. Biol. Chem.* 267: 17234-17240). Searching for this sequence of VEGF promoter region revealed the existence of numerous M-CAT-like elements. Accordingly, we hypothesized that VEGF may be one of the target genes regulated by RTEF-1.

Figure 2:
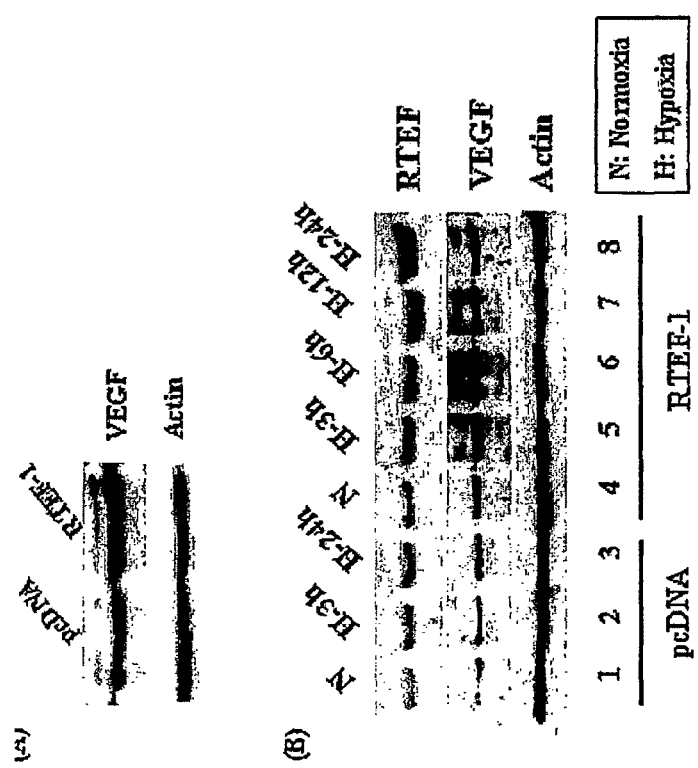
FIG. 2A is a photograph of a Western blot showing an increase in VEGF expression in RTEF-1-transfected BAEC cells as compared to BAEC cells transfected with equal amounts of control vector (pcDNA3.1/GS).
FIG. 2B is a photograph of a Western blot showing RTEF-1 and VEGF protein expression at various time points of hypoxia in BAEC cells transfected with (lanes 1-3) or without (lanes 4-8) RTEF-1. VEGF expression is stimulated under conditions of hypoxia to a greater extent when RTEF-1 is overexpressed simultaneously. Note, hypoxia, per se, increases VEGF expression, but overexpression of RTEF-1 upregulates the VEGF expression.
Figure 3:
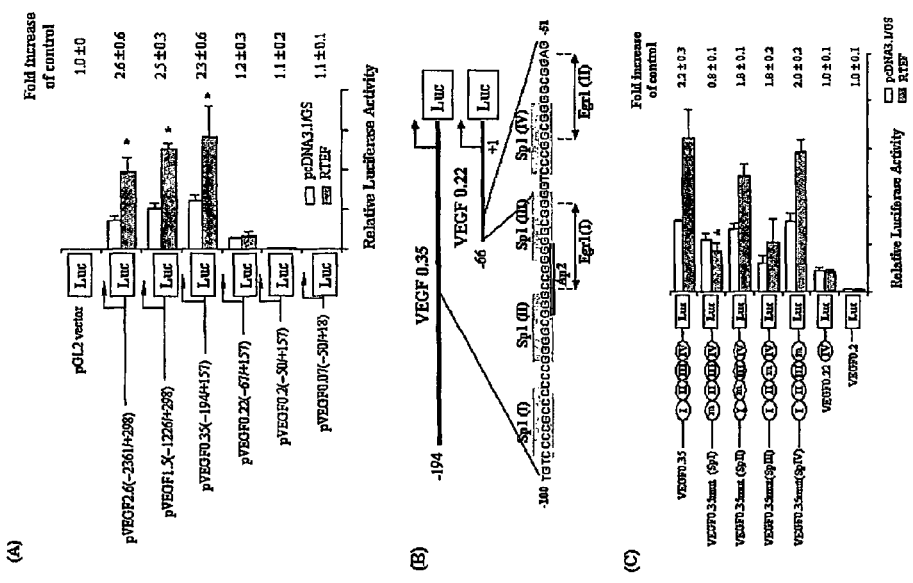
FIG. 3A is a schematic diagram showing various truncated VEGF promoters operably linked to a luciferase reporter gene and the promoter activity associated with each mutant. Transient transfection assays were performed using a set of truncated VEGF promoter Luc constructs (1.00 µg) and control vector pcDNA3.1/GS (0.5 ug, open bar) or equal amount of RTEF-1 cDNA (black bar). pcDNA4.0TO/lacZ (0.01 µg) was co-transfected to correct the transfection efficiency. This figure shows that the region responsible for RTEF-1-mediated VEGF promoter activity is located between VEGF 0.35 to VEGF 0.22. Data are expressed as means±S.E. of three separate experiments. *P<0.05, compared to pcDNA3.1/GS transfected cells in each individual construct.
FIG. 3B is a schematic diagram showing the consensus sequence of transcription factor binding sites (Sp1, Egr1, and AP2 elements) in the VEGF promoter sequence of −100/−50 (SEQ ID NO: 4).
FIG. 3C is a bar graph showing the transcriptional activation of mutant Luc constructs transfected into BAEC in the presence or absence of RTEF-1. 1 µg of wild, mutated, or deleted VEGF 0.35 constructs was cotransfected with 0.5 µg pcDNA3.1/GS or RTEF-1 cDNA in BAEC cells. Luciferase activity was determined after 48 hours of transfection. Transfection efficiency was corrected with the amount of expressing input pcDNA4.0TO/LacZ. The significant reduction in RTEF-1-induced VEGF promoter activity was observed only upon mutation of the Sp1-I sequence. Data are expressed as means±S.E. of three separate experiments. *P<0.05, compared to pcDNA3.1/GS transfected cells in each individual construct.

To investigate this hypothesis, the region of the VEGF promoter required for RTEF-1 regulation was determined in BAEC cells using a series of truncated VEGF promoter constructs (see FIG. 2). Overexpression of RTEF-1 in BAEC cells resulted in a greater than two-fold activation of the VEGF promoter activities in three different sequences of the VEGF promoter: VEGF 2.6 (−2361/+298), VEGF 1.5 (−1226/+298), and VEGF 0.35 (−194/+157) promoter activity (FIG. 3A). However, deletion of the VEGF promoter sequence from 2.6 Kb to 0.35 Kb did not affect the transcriptional activity of RTEF-1. In contrast, deletion of the region between VEGF 0.35 (−194/+157) and VEGF 0.22 (−66/+157) abolished the RTEF-1-mediated effect (FIG. 3A). These findings suggest that the possible gene-regulatory elements within the VEGF promoter necessary for RTEF-1 activation are located between −194 and −66 of the VEGF promoter sequence. Interestingly, none of the M-CAT elements predicted to exist within the VEGF promoter was found in this region. However, there are three consensus stimulating protein 1 (Sp1) elements, one transcription factor early-growth-response 1 gene product (Egr-1) elements, and two activator protein 2 (AP2) elements found in the −194/−66 region of the VEGF promoter sequence (FIG. 3B).

Example 3

Dose-Dependent Upregulation of VEGF Expression by RTEF in BAEC Cells

Figure 4:
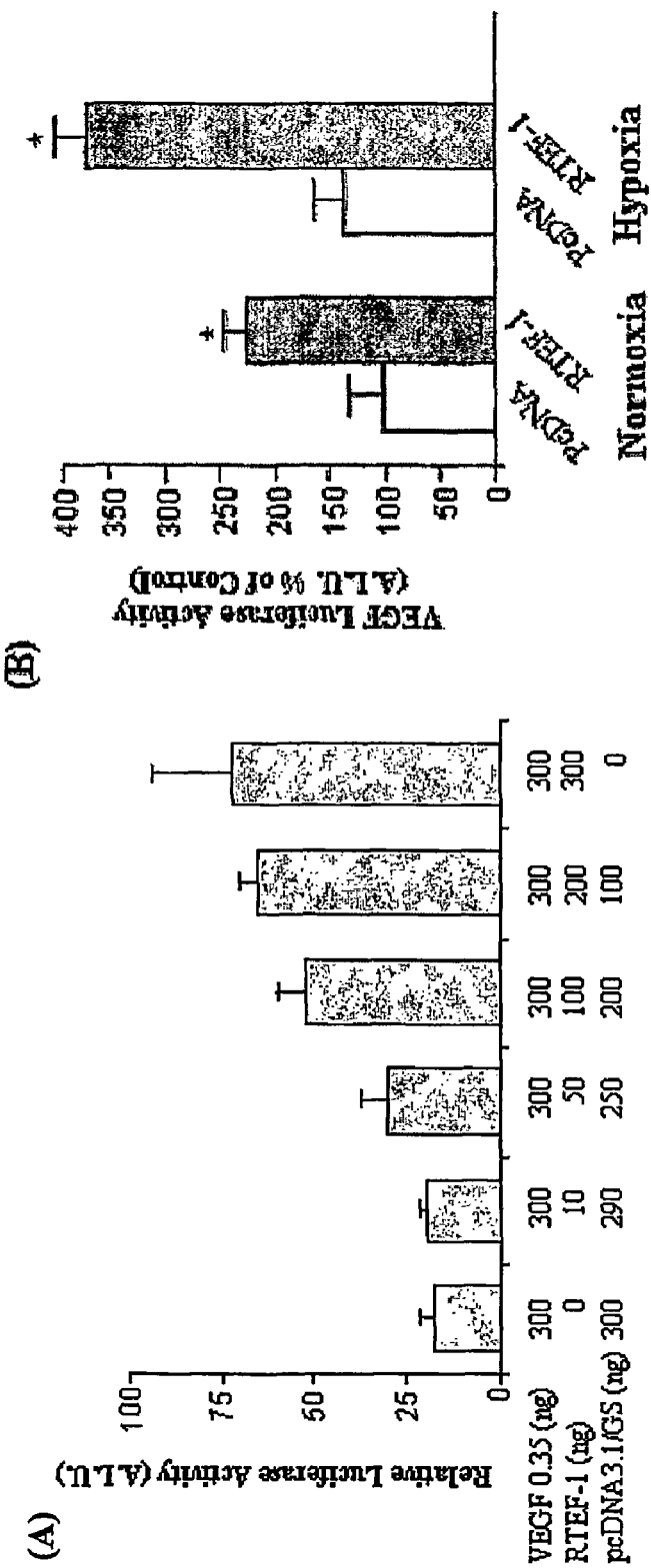
FIG. 4A is a bar graph showing the activity of the VEGF promoter (as measured by luciferase activity) in the presence of increasing amounts of RTEF-1. 300 ng of VEGF 0.35 construct was cotransfected with various combinations of pcDNA3.1/GS and RTEF-1 (final total amount=300 ng) in BAEC cells. Luciferase activity was determined after 48 hours of transfection. VEGF promoter activity is increased along with increasing amounts of RTEF-1. Data are expressed as means±S.E. of three independent experiments.
FIG. 4B is a bar graph showing the activity of the VEGF promoter (as measured by luciferase activity) in the presence of absence of RTEF-1 under normoxic or hypoxic conditions. BAEC were transfected with control vector (1.0 µg of pcDNA3.1/GS (open bar)) or an equal amount of RTEF-1 (closed bar) and VEGF promoter constructs (0.5 µg). Transfected cells were fasted and incubated under either normoxic or hypoxic conditions for 6-8 h after 16 h of transfection. Luciferase activity was then determined. RTEF-1 significantly stimulated VEGF promoter activity in BAEC cells exposed to hypoxic conditions. The data are expressed as percentages of pcDNA3.1/GS transfected cells as control using the means±S.E. of three independent experiments. *, p<0.05.
Figure 5:
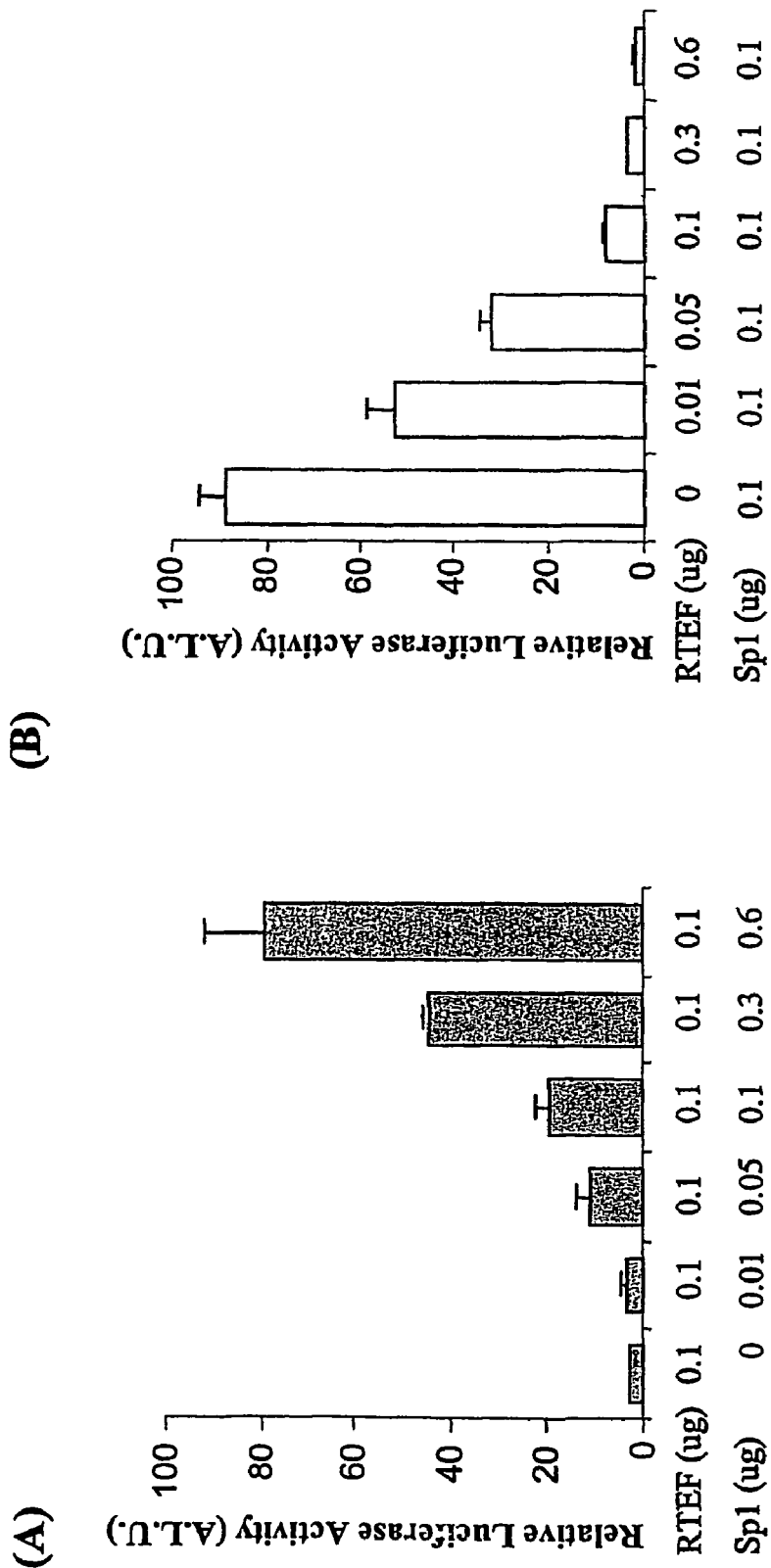
FIG. 5A is a bar graph showing the activity of the VEGF promoter (as measured by luciferase activity) in the presence of RTEF-1 and increasing amounts of Sp1-containing VEGF promoter construct cDNA.
FIG. 5B is a bar graph showing the activity of the VEGF promoter (as measured by luciferase activity) in the presence of Sp1-containing VEGF promoter construct cDNA and increasing amounts of RTEF-1.

The identified putative target region within the VEGF promoter for RTEF-1-mediated transcriptional activation was further analyzed by performing a dose-dependent induction of VEGF promoter activity by RTEF-1 in BAEC cells. To determine that RTEF-1 stimulates VEGF on its transcriptional level, the activities of a luciferase construct under the control of a VEGF promoter were measured. As shown in FIG. 4A, BAEC cells were transiently cotransfected with 300 ng of VEGF 0.35, and various doses of RTEF-1 and pcDNA 3.0, such that the total amount of DNA was 600 ng. As the level of RTEF increased, we observed a concomitant stimulation of VEGF 0.35 in BAEC, as determined by a 2.2+/−0.3-fold increase in luciferase activity. Furthermore, RTEF-1 transactivated the VEGF promoter in a dose-dependent manner. In addition, compared with normoxia, exposure of BAECs cotransfected with VEGF promoter construct and RTEF-1 cDNA to hypoxia revealed a 2.7+/−0.2-fold increase in promoter activity, as determined by an increase in luciferase activity (see FIG. 4B). Our results therefore confirm that the responsible region within the VEGF promoter for RTEF-1 regulation is located between −194/+157 and that the level of RTEF-1 correlates with the level of transcriptional activity of the VEGF promoter.

Example 4

VEGF Transactivation by RTEF-1 is Sp1 Dependent

The significance of Sp1 clusters in close proximity to the transcription start site has previously been demonstrated for the VEGF promoter (Patterson et al., *J. Biol. Chem.* (1995) 270:2311-23118 and Patterson et al., *J. Biol. Chem.* (1997) 272:8410-8416). Four adjacent Sp1 consensus binding sites have been identified between the sequence of −100/−51 (FIG. 3B). To test whether any of the four GC-rich Sp1 consensus elements is the target domain for RTEF-1, mutant Sp1 domain-containing luciferase constructs were created and transfected into BAEC cells. The constructs comprised VEGF 0.35 mutant (Sp1-I, −97 to −90), VEGF 0.35 mutant (Sp1-II, −86 to −79), and VEGF 0.35 mutant (Sp1-III, −75 to −68), in which critical two-nucleotide mutations were incorporated within the core Sp1 binding sites, and the shorter luciferase construct VEGF 0.22, which contains Sp1-IV and Egr1-II sites. As shown in FIG. 3C, analyses of the VEGF 0.35 mutant constructs, the VEGF 0.22 construct, and the VEGF 0.2 construct indicated that only VEGF 0.35 mutant (Sp1-I) lacked luciferase activity when stimulated by RTEF-1. These data suggest that VEGF transactivation by RTEF-1 is Sp1-dependent, and that the Sp1-I-binding domain (−97 to −87) of the VEGF promoter is required for the stimulation of RTEF-1.

Example 5

Sp1-I is the Key Element to Induce VEGF Promoter Activity by RTEF-1

Figure 6:
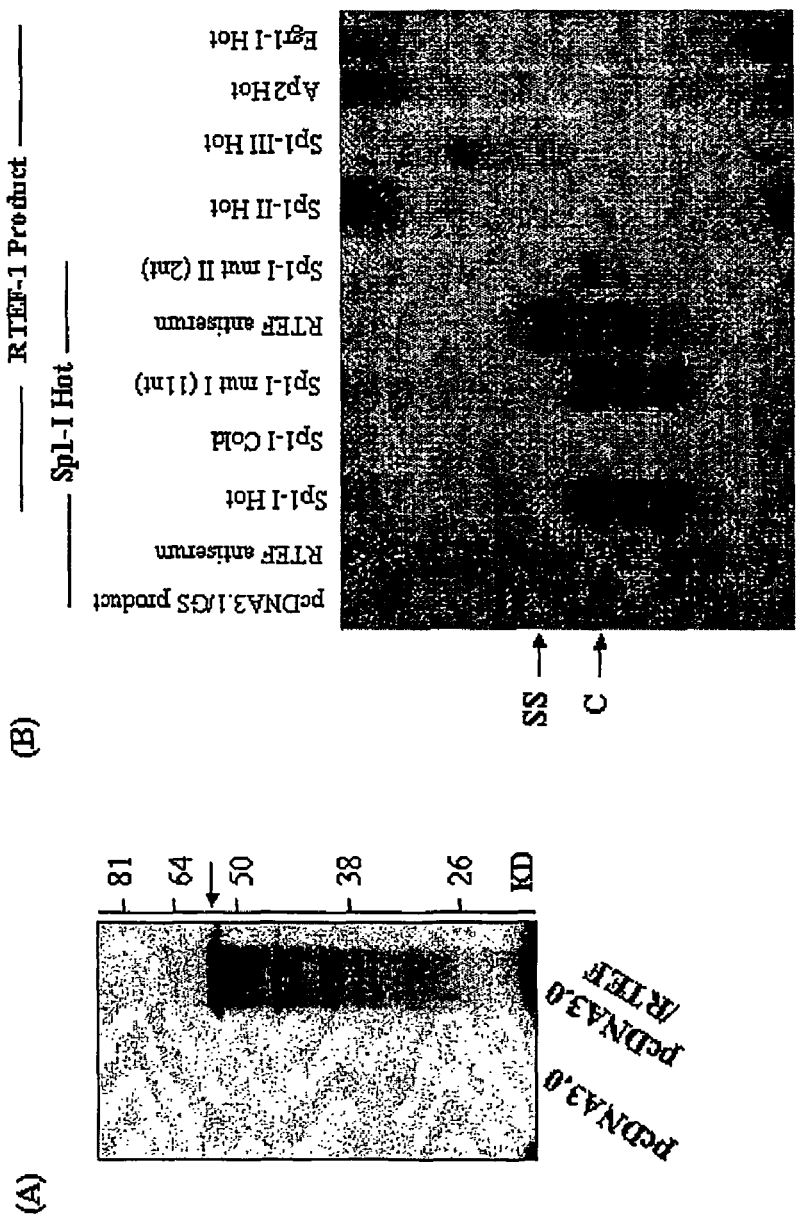
FIG. 6A is a picture showing the translated protein product of RTEF-1 after $^{35}S$ labeling. In vitro transcription/translation reactions using the TNT reticulocyte lysate kit (Promega Madison, Wis.) were performed with 1 µg cDNA according to manufacturer's protocol. The arrow indicates the position of the RTEF-1 product.
FIG. 6B is a picture representing electrophoretic mobility shift assays to detect which Sp1 site within the VEGF promoter RTEF-1 binds to. In vitro translated pcDNA3.1/GS (lane 1) and RTEF-1 product were incubated with hot VEGF Sp1-I oligonucleotide (lane 3), cold Sp1-I (lane 4), complete mutated (11 nt) or two nucleotides mutated Sp1-I (Mut I for lane 5 and Mut II for lane 7), or RTEF-1 antiserum (lane 6). Lane 2 represents RTEF antiserum incubated with Sp1-I hot oligonucleotides. Complex (C) indicates the complex of RTEF-1 product and Sp1-I oligonucleotide. There was no binding activity found when RTEF-1 product incubated with hot Sp1-II (lane 8), Sp1-III (lane 9), Ap2 (lane 10) and Egr1-I (lane 11). The supershift (SS) band indicates the super complex combination of RTEF-1, Sp1-I oligonucleotide, and RTEF-1 antiserum.

To identify the specific regulatory element on the VEGF promoter that is bound by RTEF-1, we performed in vitro transcription/translation labeling with $^{35}$S-methionine to express RTEF-1 product from a RTEF-1 cloned construct. As shown in FIG. 6A, the translated product of RTEF-1 cDNA generated the expected protein size of 54 KD. Next, we created a series of double-stranded oligonucleotide probes corresponding to the individual VEGF promoter Sp1 sequences for use in electrophoretic mobility shift assays (EMSA). The VEGF Sp1-I, -II, and -III oligonucleotide sequences were used to generate radiolabeled probes for use in competition assays. In addition, two mutated double-stranded oligonucleotides, in which either the Sp1 consensus sequence was substituted with tttttttttttt (Mut 1, −97/−87; SEQ ID NO: 1) or the CC of the core Sp1 sequence was substituted with tt (Mut 2, −92/−91), were used to determine the specificity of RTEF-Sp1 binding. As shown in FIG. 6B, RTEF-1 was found to bind to the Sp1-I motif on the VEGF promoter by EMSA (specified by anti-RTEF-1 antiserum, Band SS); there was no band at the same position in the Sp1-II, Sp1-III, Ap2, and Egr1-I labeled complex. This RTEF/Sp1-I complex was specific because it was repressed by the addition of excessive unlabeled Sp1-I oligonucleotide. Moreover, the DNA-protein complex (band C) was not eliminated by the mutant Sp1 consensus oligonucleotide (Mut 1), while the mutated core Sp1 oligonucleotide (Mut 2) was able to compete with hot Sp1-I oligonucleotides for binding to the RTEF-1 product, thereby out-competing some of the DNA-protein complex labeled band. No DNA-protein complex was identified when mutated Sp1 consensus oligonucleotide (Mut 1) was used as a probe.

Supershifts were conducted with antiserum to RTEF-1. The addition of the RTEF-specific antiserum supershifted the complex (band SS) binding to the Sp1-I oligonucleotide, indicating that the DNA-protein complex contained the RTEF product.

The physical interaction of RTEF-1 on the VEGF promoter was further examined by a chromatin immunoprecipitation assay. Chromatin fragments from BAEC transfected with pcDNA3.1/GS or RTEF-1 DNA were immunoprecipitated with or without RTEF-1 antiserum. The immunoprecipitated DNA was isolated and subjected to PCR analysis using primers specific to the putative Sp1-binding domain on the proximal portion of VEGF promoter. As illustrated in FIG. 6C, an expected 250-bp DNA fragment was amplified in samples containing total input chromatin or RTEF-1 immunoprecipitant, but not in the control sample (mock) containing dialysis buffer, or RTEF-1 antiserum-free sample, suggesting that RTEF-1 binds to this highly GC-rich sequence containing the Sp1 domains on the proximal portion of VEGF promoter to regulate VEGF expression. Furthermore, the intensity of amplified DNA fragment is higher in RTEF-1 than in pcDNA3.1/GS transfected cells. This indicates that the expression of VEGF increases synchronously with the amount of RTEF-1.

Example 6

RTEF-1 Enhances VEGF Expression Additionally in Hypoxia

Figure 7:
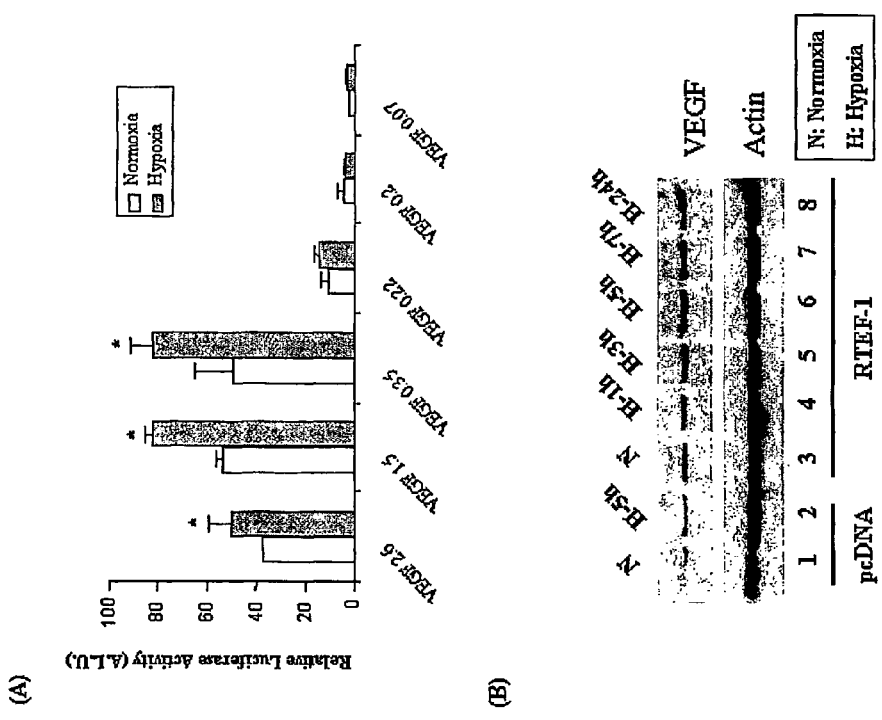
FIG. 7A is a bar graph showing the activity of various truncated VEGF promoters (as measured by luciferase activity) in normoxic and hypoxic conditions. BAEC cells were transfected with control vector (0.5 µg pcDNA3.1/GS, as shown by the open bar) or RTEF-1 (0.5 µg, as shown by the black bar) and a set of truncated VEGF promoter constructs (1.0 µg). Transfected cells were fasted and either incubated in normoxia or hypoxia for 6-8 hours after 16 hours of transfection, after which luciferase activity was determined. As indicated, RTEF-1 stimulated VEGF promoter activity up to about 1.5 fold in hypoxia. Data are expressed as means±S.E. of three independent experiments. *P<0.05, compared to pcDNA3.1/GS transfected cells in each individual construct.
FIG. 7B is a series of pictures showing the protein expression of VEGF in hypoxic and normoxic conditions in the presence or absence of RTEF-1. As shown, RTEF-1 expression was stimulated under hypoxic conditions as early as one hour and kept increasing up to seven hours, but was downregulated back to normal levels after 24 hours. VEGF expression was induced synchronously with RTEF-1 expression, but its expression remained high till 24 hours in hypoxic RTEF-1 transfected cells.

To determine the functional importance of RTEF-1 in stimulating the transcriptional activity of the VEGF promoter, we next investigated the effect of RTEF-1 on VEGF promoter activity under hypoxic conditions. FIG. 7A shows that RTEF-1 enhanced VEGF promoter activity in hypoxia relative to normoxia. Following a 6 hour exposure of RTEF-1-transfected BAEC to hypoxia, VEGF transcriptional activity was enhanced in the following VEGF promoter constructs: 2.6, 1.5 and 0.35. In contrast, the same activity was not observed with the shorter constructs, which were not associated with any significant increase in VEGF promoter activity. These studies confirm the inducible nature of the RTEF-1 in response to hypoxia and further support the role of RTEF-1 in regulating VEGF expression particularly under hypoxic conditions.

We also examined the effect of RTEF-1 on VEGF protein expression in hypoxia. Under hypoxic conditions, we found that the expression of VEGF protein increased synchronously with RTEF-1 in RTEF-1-transfected cells in a time-dependent fashion. VEGF expression increased as early as one hour, reached its maximum expression after 5 hours, and maintained such expression up to 24 hours. This suggests that RTEF-1 expression is linked to hypoxia-induced VEGF expression. As shown in FIG. 7B, the expression of VEGF in the presence of RTEF-1 (lane 6) is much higher than in the absence of RTEF-1 (lane 2), after 5 hours hypoxia.

Example 7

Effect of RTEF-1 in Angiogenesis

Figure 8:
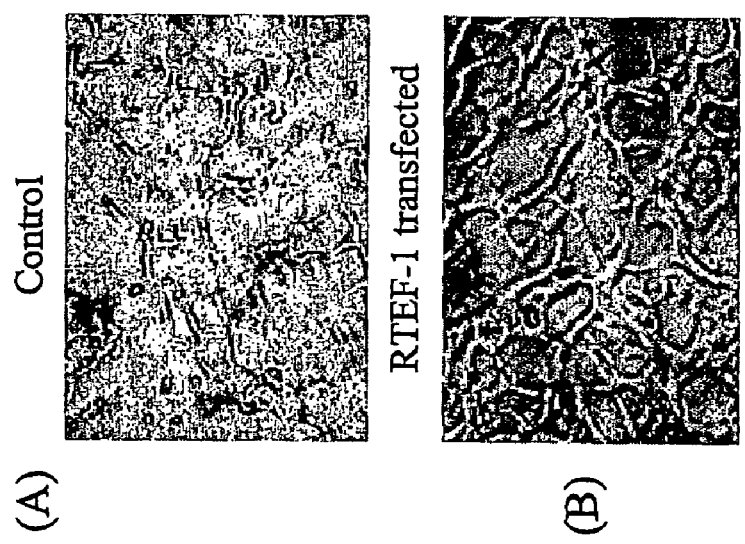
FIG. 8A is a photograph showing the effect of an in vitro MATRIGEL® assay involving wild-type BAEC cells. Wild-type BAEC cells were plated on growth factor-reduced MATRIGEL® and cultured with serum-free Dulbecco's modified Eagle's medium and tested for [$^3$H]thymidine incorporation.
FIG. 8B is a photograph showing the effect on cell growth in an in vitro MATRIGEL® assay involving RTEF-1-transfected BAEC cells. RTEF-1-overexpressing cells demonstrated a markedly faster growth rate compared to BAEC wild-type or vector-transfected cells based on [$^3$H]thymidine incorporation, especially under hypoxic conditions. Note that ring and cord formation were observed in RTEF-stably transfected BAEC but not in control cells after 48 hours of culture (compare with FIG. 8A).

After determining that RTEF-1 binding to the VEGF promoter increased VEGF expression, we measured the ability of RTEF-1 to accelerate the proliferation of cell growth and formation of vascular structure (e.g., the ability of RTEF-1 and its derivatives to induce angiogenesis via transactivation of VEGF). BAEC cells overexpressing RTEF-1 demonstrated a markedly faster growth rate compared with BAEC wild type or vector-transfected cells as determined by [$^3$H]thymidine uptake, especially under hypoxic conditions (see FIGS. 8A and 8B). In addition, the presence of visible ring and cord formation in RTEF-1 stably transfected BAEC but not in control cells after 48 hours of culture on growth factor-reduced MATRIGEL® confirms that RTEF-1 can accelerate the formation of vascular structures in the absence of serum after 24-48 h (compare FIG. 8A to 8B).

Example 8

RTEF-1 Regulates FGFR1 Expression in Endothelial Cells

Figure 9:
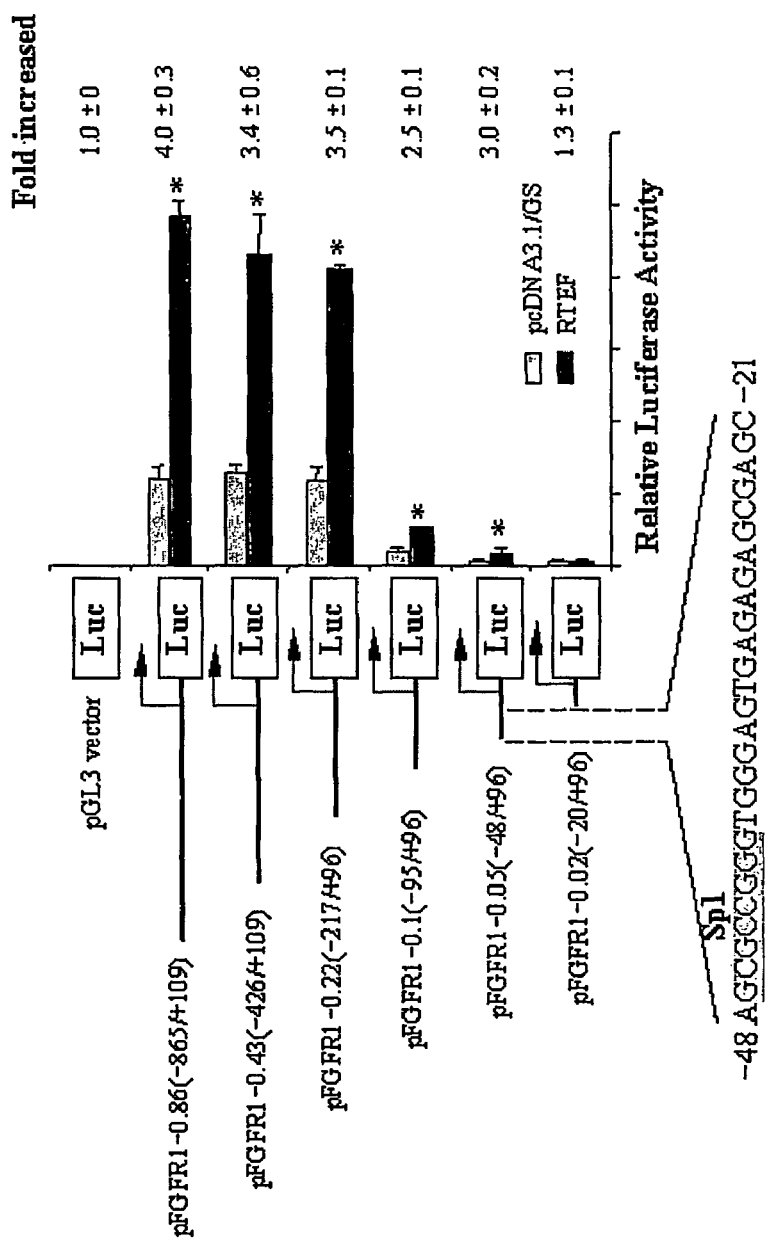
FIG. 9 is a schematic diagram showing various truncated FGFR1 promoters operably linked to a luciferase reporter gene and the promoter activity associated with each mutant. Transient transfection assays were performed in BAEC cells using a set of truncated FGFR1 promoter Luc constructs and control vector pcDNA3.1/GS or an equal amount of RTEF-1 cDNA. The activity of FGFR1 promoter constructs, 0.99 kb, 0.44 kb, 0.28 kb, and 0.15 kb (−48~+94 related to the 5' transcriptional starting site) was found to increase over three fold in the presence of RTEF-1, but almost no stimulated activity was observed on the 0.12 kb construct (−20~+94). RTEF-1 binding of the FGFR1 promoter was associated with the −48 to −21 region of the FGFR1 promoter (SEQ ID NO: 5).
Figure 10:
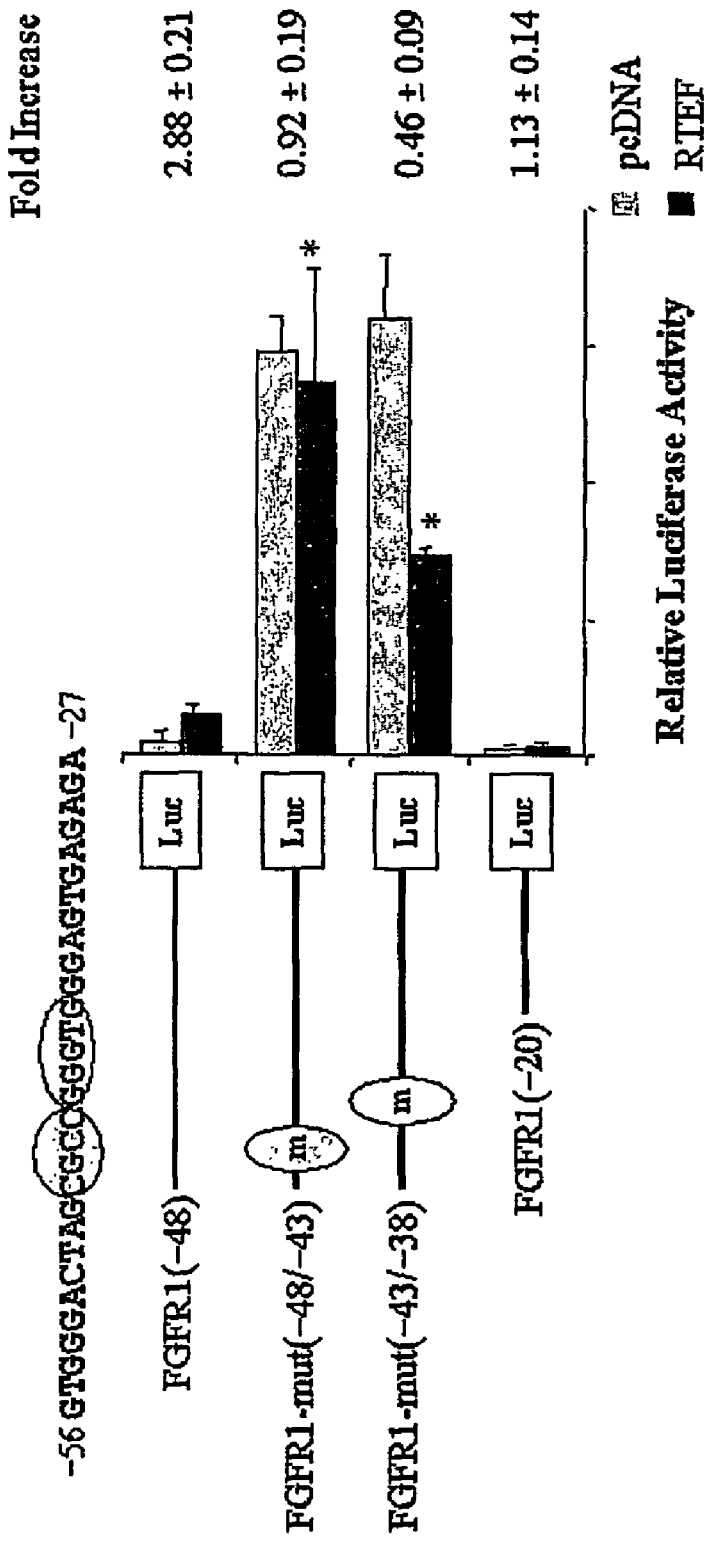
FIG. 10 is a schematic diagram showing deletion and mutation analysis of the 0.15 kb FGFR1 promoter (−48/+94). The sequence between −48 and −20 of the FGFR1 promoter contains a stimulating protein (SP)-1 like element and is responsible for the RTEF-1 protein binding (SEQ ID NO: 6). Interestingly, there is no M-CAT related binding element found within this region.

Members of the fibroblast growth factor receptor (FGFR) family mediate cellular signaling following binding of their ligand, FGF. Activation of the FGFR upon FGF binding results in, e.g., myoblast proliferation and a delay in myoblast differentiation. In skeletal muscle, expression of FGFR1 has been shown to be a positive regulator of proliferating myoblasts. The expression of FGFR1 declines during differentiation of the myoblasts. Studies have also shown that FGFR1 is critical for promoting the development and differentiation of cardiac and somatic muscle cells. FGFR1 is has also been shown to be involved in cardiogenesis. Our studies demonstrate that RTEF-1 is up-regulated in hypoxic endothelial cells and that over-expression of RTEF-1 increases FGFR1 promoter activity. RTEF-1 is a member of TEF-1 family, which is involved in the regulation of cardiac and skeletal muscle cell-specific genes through M-CAT elements on their promoters. We determined that RTEF-1 acts as a trans-regulator and binds to cis-elements of the FGFR1 promoter to increase FGFR1 gene expression. Co-transfection of BAEC cells with a RTEF-1 cDNA construct and various different FGFR1 promoter-luciferase constructs revealed the region of activity associated with RTEF-1 binding of the FGFR1 promoter was associated with the −48 to −21 region of the FGFR1 promoter. The activity of the FGFR1 promoter constructs, 0.99 kb, 0.44 kb, 0.28 Kb, and 0.15 kb (−48~+94 related to 5' transcriptional starting site), was found to increase over three fold in the presence of RTEF-1, but almost no stimulated activity on 0.12 kb (−20~+94) construct (FIG. 9). Deletion and mutation analysis of the 0.15 Kb FGFR1 (−48/+94) promoter resulted in the identification of a sequence containing a stimulating protein (SP)-1-like element that is responsible for RTEF-1 product binding (FIG. 10). Interestingly, there is no M-CAT related binding element found at this region.

Example 9

RTEF-1 Regulates COX-2 Expression in Endothelial Cells

Cyclooxygenase (COX) is a key regulatory enzyme in eicosanoid metabolism, which converts free arachidonic acid to $PGH_2$. Prostaglandins mediate inflammation locally and modulate physiological responses systemically. COX-2 is one of two identified isoforms of COX that is induced upon cell activation and is generally not present or is present minimally in most tissues. The expression of COX-2 is more often associated with inflammation and other pathophysiological states. Inhibition of COX-2 expression has been shown to aggravate doxorubicin-mediated cardiac injury in vivo.

Figure 11:
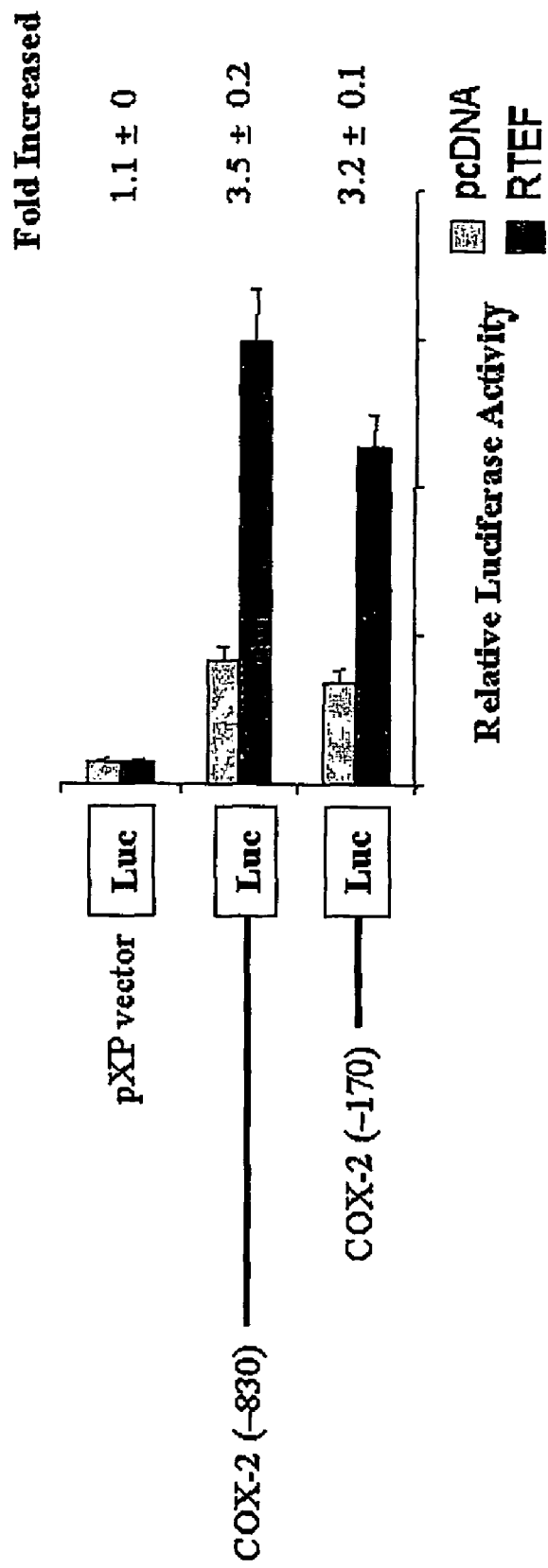
FIG. 11 is a schematic diagram showing various truncated COX-2 promoters operably linked to a luciferase reporter gene and the promoter activity associated with each mutant. Transient transfection assays were performed in BAEC cells using a set of truncated COX-2 promoter Luc constructs and control vector pcDNA3.1/GS or an equal amount of RTEF-1 cDNA. The activity of the COX-2 promoter was found to increase over three fold in BAEC cells in the presence of RTEF-1.
Figure 12:
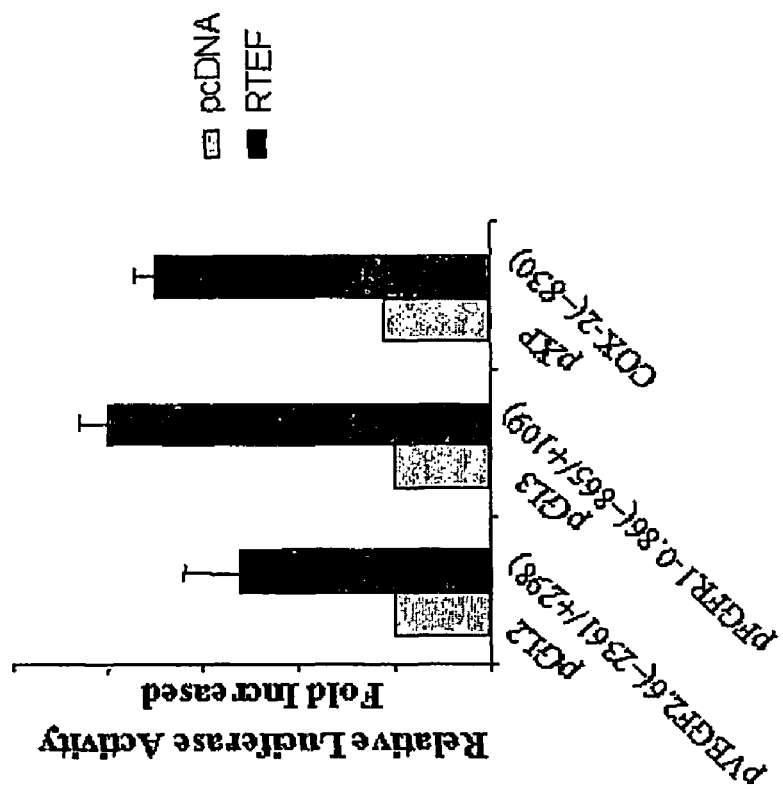
FIG. 12 is a graph showing the effect of RTEF-1 on transactivation of the VEGF, FGFR1, and COX-2 promoters as a function of luciferase activity in BAEC cells transfected with the indicated cDNA, relative to luciferase activity in BAEC cells transfected with control pcDNA3.1/GS.

The use of COX-2 inhibitors has been shown to result in an increased incidence of cardiovascular damage and worsening heart failure. Our studies show that RTEF-1 also stimulates COX-2 promoter activity over three fold in endothelial cells (FIG. 11). FIG. 12 demonstrates the effect of RTEF-1 on transactivation of the VEGF, FGFR1, and COX-2 promoters as a function of luciferase activity in BAEC cells transfected with the indicated cDNA, relative to luciferase activity in BAEC cells transfected with control pcDNA3.1/GS.

Example 10

In Vivo Administration of RTEF-1 in a Myocardial Infarction Mouse Model Via Recombinant Adenovirus A recombinant adenovirus construct in association with green fluorescent protein (rAV.RTEF-1.GFP) that is under the control of the human cytomegalovirus (CMV) promoter can be used to express RTEF-1. This recombinant adenovirus virus construct also comprises part of the α-MHC promoter fragment as a cardiac myocyte targeting probe, and part of human growth hormone cDNA sequence as a spotting marker. A cell lysate containing concentrated rAV.GFP (control) or rAV.RTEF-1.GFP ($10^{8-12}$ PFU/ml) is applied to BAEC cells, which are subsequently assayed for RTEF-1 recombinant adenovirus function in vitro. Purified rAV.RTEF-1.GFP can also be injected into the infracted myocardial area of mouse heart to assay the physiological effects of RTEF-1 expression on the relative angiogenic factors in vivo.

Example 11

It Vivo Treatment of Patients with Recombinant Adenovirus or Adeno-Associated Virus Patients diagnosed with coronary artery disease or peripheral vascular disease can be treated using in vivo methods consisting of administration of a recombinant adenovirus (Ad) or adeno-associated virus (AAV) containing a human RTEF-1 cDNA. In vivo therapy involves transfection of a RTEF-1 nucleic acid directly into the cells of a recipient host without the need for prior removal of those cells from the recipient host.

In vivo delivery is desirably accomplished by (1) infusing an adenovirus or adeno-associated virus vector construct into a blood vessel that supplies a diseased area of a patient's body (e.g., an occluded artery), or (2) injecting an adenovirus or adeno-associated virus vector construct directly into a diseased tissue of the patient (e.g., an ischemic tissue). In an especially desired in vivo embodiment, a catheter is inserted into a blood vessel in the neck of an organism and the tip of the indwelling catheter is advanced with fluoroscopic guidance to a position in an artery that requires treatment or near a tissue to be treated. It is desired that the tip of an indwelling catheter be placed in proximity to an area of the artery or tissue that contains the cells to be transfected. The Ad or AAV can also be directly targeted to specific cells using cell-specific surface antigens, although this is not required. Adenovirus or adeno-associated virus is administered to patients desirably by means of intravenous administration in any suitable pharmacological composition, either as a bolus or as an infusion over a period of time. Injection of the recombinant virus directly into the tissue, or into a blood vessel that supplies the tissue, to be treated, or into a blood vessel that requires treatment, will promote incorporation of the human RTEF-1 cDNA into the targeted cells (e.g., vascular endothelial cells), which, upon expression of RTEF-1, will promote activation of VEGF, FGFR, or COX-2 and will increase vascularization (e.g., neovascularization or angiogenesis).

After delivery of an adenovirus or adeno-associated virus vector construct to the targeted cells or tissue of the patient, the cells are maintained under physiological conditions and for a period of time sufficient for the adenovirus or adeno-associated virus vector construct to infect the targeted cells. Additional incubation time can be provided to allow expression of the RTEF-1 polypeptide in the transfected cells.

Physiological conditions are those necessary for viability of the targeted cells and include conditions of temperature, pH, osmolality and the like. In a desired embodiment, temperature is from about 20° C. to about 50° C., more desirably from about 30° C. to about 40° C. and, even more desirably about 37° C. pH is preferably from about a value of 6.0 to a value of about 8.0, more desirably from about a value of about 6.8 to a value of about 7.8 and, most desirably about 7.4. Osmolality is desirably from about 200 milliosmols per liter (mosm/L) to about 400 mosm/l and, more desirably from about 290 mosm/L to about 310 mosm/L. Other physiological conditions needed to sustain cell viability are well known in the art.

A time period sufficient for expression of a RTEF-1 polypeptide in a targeted cell, e.g., a vascular endothelial cell, varies inter alia, as is well known in the art, on the type of adenovirus or adeno-associated virus vector used and the method of delivery. It should also be pointed out that because that the adenovirus or adeno-associated virus vector employed may be replication defective it may not be capable of replicating in the cells that are ultimately infected.

An adenovirus or adeno-associated virus vector construct is typically delivered in the form of a pharmacological composition that comprises a physiologically acceptable carrier and the adenovirus or adeno-associated virus vector construct. An effective amount of an adenovirus or an adeno-associated virus vector construct is delivered, and consists of 5 pfu/cell, 10 pfu/cell, or 20 pfu/cell, or any other amount that is effective for promoting expression of a RTEF-1 polypeptide in the target cells. Means for determining an effective amount of an adenovirus or an adeno-associated virus vector construct are well known in the art.

As is well known in the art, a specific dose level for any particular recipient depends upon a variety of factors including the infectivity of the adenovirus or adeno-associated virus vector, the age, body weight, general health, sex, diet, time of administration, route of administration, rate of excretion, and the severity of the disease condition of the recipient. Gene therapy methods for administering proteins, such as RTEF-1, are reviewed in, e.g., Khan et al. (Gene Therapy 10:285-291, 2003).

Example 12

Combination Therapy Using RTEF-1 and HIF-1α

Hypoxia changes many endothelial cell properties including directly regulating many genes, especially by increasing cellular levels of hypoxia-inducible factor (HIF)-1α, which in turn amplifies the expression of angiogenesis-related genes, such as VEGF and VEGF receptor-1 (VEGFR-1), basic fibroblast growth factor 2, and angiopointin-1, suggesting that hypoxia is an important stimulator for the formation of new blood vessels in coronary artery disease, tumor angiogenesis, and diabetic neovascularization. The effect of hypoxia-associated gene regulation in angiogenesis is dependent on several transcription factors for the activation of targeting genes.

Therefore, the in vivo treatment discussed in Example 11 can be modified to be a combination therapy that involves the additional administration of an adenovirus or an adeno-associated virus vector construct that contains a human HIF-1α cDNA. The administration of both RTEF-1 and HIF-1α to a patient synergistically acts to promote, e.g., VEGF transactivation, thereby resulting in a promotion in vascularization in a patient in need thereof.

The above experiments were performed using the following methods and materials.

Methods and Materials

Cell Cultures and Transfection

The bovine arotic endothelial cells (BAEC) were cultured in Dulbecco's modified Eagle's medium (DMEM), supplemented with 10% fetal calf serum, 100 µg/ml streptomycin and 100 U/ml penicillin, at 37° C. in a 95% air+5% $CO_2$ atmosphere. Cells were transfected with DNA (1 µg/$10^5$ cells) using the Lipofectamine method according to the manufacturer's protocol (Invitrogen, Carlsbad, Calif.) and as described previously (Amer. J. Physiol. Gastrointest. Liver Physiol. 279:G806-G814, 2000). VEGF promoter Luc constructs (0.5 µg) and control vector pcDNA3.1/GS (1.0 µg) or equal amount of RTEF-1 cDNA were transfected. pcDNA/lacZ (0.01 µg) was cotransfected to confirm that the transfection efficiency was about 70 to 80 percent. After transfection, cells were incubated for an additional 48 h before analysis.

Hypoxic Incubation

Hypoxia was induced using a Modular Incubator Chamber (Billumps-Rothenberg, Del Mar, Calif.). The hypoxia chamber was filled with artificial atmosphere and the concentration of oxygen (<1%) was determined before and after incubation by using an Oxygen Analyzer (Vascular Technology, Bradford, Mass.). The hypoxia chamber containing cell-culture dishes was transferred to a culture incubator according to the time schedule of studies.

Construction of the RTEF Expression Vector and VEGF Promoter-Luc Plasmids

The full length of RTEF cDNA was obtained from Invitrogen (Carlsbad, Calif.) and subcloned into a pcDNA3.1/GS expression vector in frame. The VEGF reporter constructs, which contained sequences derived from the human VEGF promoter that were used to drive expression of the firefly luciferase gene, were kindly provided by Dr. Debabrata Mukhopadhyay (Pathology, BIDMC, Boston; see Mukhopadhyay et al., Mol. Biol. Cell 17:5629-5639, 1997). Briefly, the sequences were inserted into pGL2-Basic vector (Promega, Madison, Wis.) and named according to the length of the fragment (from the transcription start site) in the 5' and 3' directions: VEGF 2.6 (−2361/+298), VEGF 1.5 (−1226/+298), VEGF 0.35 (−194/+157), VEGF 0.2 (−50/+15), VEGF 0.07 (−50/+18). The encompassing sequence for the VEGF 0.22 (−71/+157) construct has been amplified by PCR using primers with flanking 5'-XhoI and 3'-HindIII enzyme restriction sites to facilitate directional cloning into the pGL2-Basic vector. The Sp1-I and III mutant constructs, derived from the 0.35 Kb VEGF promoter fragment using polymerase chain reaction, were inserted into pGL-2 basic luciferase expression vector (Promega, Madison, Wis.) as described (Mukhopadhyay et al., Cancer Res. 55:6161-6165, 1995). The constructs carrying two-nucleotide (2-nt) mutations (CC to tt) within the Sp1 consensus sites (−104/−50) were generated identically. Sp1-I and IV mutant constructs in pT81 vector, kindly gifted by Dr. Michael Höcker (Berlin, Germany; see Schafer et al., J. Biol. Chem. 278:8190-8198, 2003), were resubcloned into pGL-2 basic luciferase expression vector. All constructs were sequenced from the 5'- and 3'-ends to confirm orientation and sequence correctness.

[$^3$H]-Thymidine Incorporation

For [$^3$H] thymidine incorporation, BAEC cells and BAEC cells stably overexpressing RTEF-1 DNA were incubated with 1 µCi/ml [$^3$H] thymidine (20 Ci/mmol) at 37° C. for 4 h before harvesting. After washing twice with cold PBS, cells were fixed with 10% TCA at 4° C. for 30 min, rinsed with 10% TCA, solubilized with 1 N NaOH, and neutralized with HCl. Aliquots equal to 0.1 volume of the solubilized material were counted in triplicate by liquid scintillation. Dishes that contained no cells were labeled and counted to provide background counts.

Northern Blot Hybridization Analysis

Total RNA from BAEC cells was extracted using TRI Reagent (Sigma) according to the manufacturer's protocol, and was electrophoresed on a 1.3% agarose/6% formaldehyde gel. Hybridization was analyzed under stringent conditions with human RTEF-1 cDNAs radiolabelled with $^{32}$P-dCTP, using the Klenow fragment of DNA polymerase I and random oligonucleotides as primers (Promega, Madison, Wis.). The blots were washed and autoradiograms were developed after exposure to X-ray film at −70° C., using a CRONEX™ intensifying screen (DuPont, NY).

Western Blot Analysis

BAEC cells were washed twice with cold phosphate-buffered saline, lysed in cold RIPA buffer (Boston BioProducts Inc.) containing 50 mM Tris-HCl, pH 7.4, 150 mM NaCl, 1% NP-40, 0.5% sodium deoxycholate, 0.1% SDS, and cocktailed protease inhibitors (Roche). Protein concentrations were determined with the DC Protein Standard Assay (Bio-Rad, Munich, Germany). Samples were subjected to 10% SDS-PAGE and transferred to polyvinylidene fluoride membranes (Millipore Co, Bedford, Mass.) and subsequently blocked in PBS-Tween 20 containing 7.5% non-fat milk. The membranes were incubated with the indicated primary antibodies (monoclonal anti-VEGF antibody, Santa Cruz, Calif.; polyclonal anti-RTEF-1 antibody, Genemed Synthesis, Inc., South San Francisco, Calif.), followed by incubation with horseradish peroxidase-conjugated secondary antibodies (anti-mouse or anti-rabbit IgG, Calbiochem, La Jolla, Calif.). The blots were developed using the enhanced chemiluminescence (ECL) detection system according to the instructions of the manufacturer (Amersham, Arlington Heights, Ill.).

Matrigel Analysis

BD Matrigel™ Matrix Growth Factor Reduced (BD Biosciences, Bedford, Mass.) was diluted (1:1) with cold serum-free DMEM (total 100 μl per well) and coated on pre-chilled 24 well culture dish on ice. After Matrigel solidification for 30 minutes in an incubator, $5 \times 10^4$ BAEC cells transfected with pcDNA 3.1/GS or RTEF-1 were cultured in serum-free DMEM on Matrigel coated wells. After 24 to 48 h incubation, the extent of network formation was observed and photographed.

In Vitro Transcription-Translation

Full-length of human RTEF cDNA encoding the entire open-reading frames were inserted downstream of the T7 promoter into the pcDNA3/GS vector. Coupled in vitro transcription-in vitro translation reactions were performed with 1 μg of plasmid DNA using the TNT reticulocyte lysate kit (Promega Madison, Wis.) and T7 RNA polymerase as recommended by the manufacturer. The plasmid vector pcDNA3.1/GS without an insert was used as a control.

Electrophoretic Mobility Shift Assays (EMSAs)

EMSAs were performed to identify the protein binding to the regulatory elements on the VEGF promoter. In vitro-translated RTEF products or cell extracts were prepared as described above. Double-stranded oligonucleotides, corresponding to the sequence of regulatory elements, were synthesized by Invitrogen (Carlsbad, Calif.). Double-stranded oligonucleotides (500 ng) were radiolabeled by the 5' end labeled reaction in a buffer consisting of 50 mM Tris-HCl, pH 7.6, 10 mM $MgCl_2$, 10 mM 2-mercaptoethanol, 100 mM $\gamma$-$^{32}$P-dATP (NEN Life Science Products, Boston, Mass.), and 30 UT4 polynucleotide kinase (USB, Cleveland, Ohio). EMSA was carried out by incubating 5 ul of in vitro-translated products or nuclear extracts with 25000 cpm $\gamma$-$^{32}$P-labeled oligonucleotide DNA probe in a 20 μl binding reaction containing 25 mM Tris-HCl, 100 mM KCl, 0.2 mM EDTA, 10% glycerol, 5 mM DTT (dithiothreitol), and 1 mM PMSF (phenylmethylsulfonyl fluoride). After incubation at room temperature for 30 min, the samples were loaded onto a 5% polyacrylamide (acrylamide-bisacrylamide, 29:1), 0.25× Tris borate gel and electrophoresed at 25 mA for 4 h. The gel was dried and exposed to X-ray film (Marsh Bio Product, Rochester, N.Y.) at –70° C. for 18 h. For competition experiments, the in vitro-translated RTEF-1 products or nuclear extracts were preincubated with excess unlabeled wild-type or mutated double-stranded oligonucleotides before the addition of the $\gamma$-$^{32}$P-labeled oligonucleotide DNA probe. Also, a supershift assay was performed by the incubation of RTEF-1 protein/nuclear extracts and oligonucleotide mixture with RTEF-1 antiserum (Genemed Synthesis, Inc., South San Francisco, Calif.) at room temperature for 30 min before electrophoresis.

Competition of RTEF and Sp1 Binding on the VEGF Promoter

To further examine a potential interaction between RTEF and Sp1 on the VEGF promoter, BAEC cells were either transfected with VEGF 1.5-Luc, RTEF-1 cDNA and increasing amounts of Sp1 cDNA, or with increasing amounts of RTEF-1 in the presence of 0.1 μg of pCMV-Sp1 cDNA. The relative luciferase activity was analyzed 48 h after transfection.

Chromatin Immunoprecipitation Assays

Chromatin immunoprecipitation assays were performed according to the protocol from Dr. Farnham's laboratory (Weinmann et al., Mol. Cell Biol. 21:6820-6832, 2001; Eberhardy et al., J. Biol. Chem. 275:33798-33805, 2000; Eberhardy et al., J. Biol. Chem. 276:48562-48571, 2001) with the following modifications. Briefly, immunoprecipitation (IP) of transfected and formaldehyde-cross-linked BAEC cells was performed overnight at 4° C. in the presence of RTEF-1 antiserum. Fifty percent of the supernatant from the RTEF-1 antiserum-free IP was saved as "total input" chromatin and processed with the eluted IPs beginning with the reverse of formaldehyde-cross-linking. After final ethanol precipitation, the TE resuspended IP products were used as templates for PCR using two primers (5'-GCTGAGGCTCGCCTGTC-CCCGCCCC-3' (SEQ ID NO: 2) and 5'-CAAATTCCAG-CACCGAGCGCCCTGG-3' (SEQ ID NO: 3)). These two primers were designed according to the sequences 5' and 3', respectively, to the putative Sp1 binding domain on the proximal portion of the VEGF promoter. 1× dilution buffer was used as a negative control (mock) for PCR.

Statistics

Results were expressed based on triplet experiments as mean±S.E. Statistical analysis was performed using ANOVA and Student's t-test. A p-value of <0.05 was considered to be statistically significant.

All Embodiments

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of increasing angiogenesis in a mammal comprising providing within or adjacent to tissue in need thereof in said mammal a therapeutically effective amount of Related Transcriptional Enhancer Factor-1 (RTEF-1) polypeptide or a nucleic acid molecule encoding said polypeptide, wherein said RTEF-1 polypeptide has at least 85% sequence identity to the sequence of SEQ ID NO: 7, and wherein said RTEF-1 polypeptide increases angiogenesis in said tissue of said mammal, relative to a mammal that is not administered said RTEF-1 polypeptide or said nucleic acid molecule encoding said polypeptide.

2. The method of claim 1, wherein said RTEF-1 polypeptide has at least 90% sequence identity to the sequence of SEQ ID NO:7.

3. The method of claim 1, wherein said RTEF-1 polypeptide is provided to said mammal by administering to said mammal a cell, tissue, or organ that contains said polypeptide in a therapeutically effective amount.

4. The method of claim 2, wherein said RTEF-1 polypeptide has at least 95% sequence identity to the sequence of SEQ ID NO:7.

5. The method of claim 4, wherein said RTEF-1 polypeptide comprises the sequence of SEQ ID NO:7.

6. The method of claim 1, wherein said tissue is ischemic or hypoxic.

* * * * *

UNITED STATES PATENT AND TRADEMARK OFFICE
CERTIFICATE OF CORRECTION

| | |
|---|---|
| PATENT NO. | : 7,850,959 B2 |
| APPLICATION NO. | : 10/575127 |
| DATED | : December 14, 2010 |
| INVENTOR(S) | : Li et al. |

It is certified that error appears in the above-identified patent and that said Letters Patent is hereby corrected as shown below:

On the title page, Item 56, under OTHER PUBLICATIONS, in Stewart et al., replace "vol. 36" with --vol. 37--.

Column 3, Lines 62, replace "In an embodiment of all of aspects" with --In an embodiment of all of the aspects--.

Column 6, Lines 54-55, replace "that reduces the reduces" with --that reduces--.

Column 12, Line 29, replace "condition The" with --condition. The--.

Column 13, Lines 41-42, replace "in the presence of absence of RTEF-1" with --in the presence or absence of RTEF-1--.

Column 19, Line 10, replace "SRI)" with --(MRI)--;

Line 20, replace "(I," with --(MRI),--.

Column 20, Line 30, replace "fall-length" with --full-length--.

Column 22, Lines 39-40, replace "by at least 10%, %, but possibly even 100% or more" with --by at least 10%, but possibly even 100% or more--.

Column 25, Lines 13-14, replace "is less tissue specific" with --are less tissue specific--.

Column 32, Line 54, replace "FGFR1 is has" with --FGFR1 has--.

Column 34, Lines 56-57, replace "because that the adenovirus" with --because the adenovirus--.

Column 35, Line 44, replace "arotic" with --aortic--.

Signed and Sealed this
Twenty-eighth Day of February, 2012

David J. Kappos
*Director of the United States Patent and Trademark Office*